(12) United States Patent
Ghoshal et al.

US007202092B2

(10) Patent No.: US 7,202,092 B2
(45) Date of Patent: Apr. 10, 2007

(54) INDINAVIR DERIVATIVES USEFUL IN IMMUNOASSAY

(75) Inventors: Mitali Ghoshal, Noblesville, IN (US); Gerald Sigler, Carmel, IN (US); Aniruddha P. Patwardhan, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 309 days.

(21) Appl. No.: 10/988,477

(22) Filed: Nov. 12, 2004

(65) Prior Publication Data

US 2005/0148596 A1 Jul. 7, 2005

Related U.S. Application Data

(63) Continuation-in-part of application No. 10/669,831, filed on Sep. 24, 2003, now abandoned, which is a continuation-in-part of application No. 10/192,052, filed on Jul. 10, 2002, now abandoned.

(60) Provisional application No. 60/305,192, filed on Jul. 13, 2001.

(51) Int. Cl.
  *G01N 33/546* (2006.01)
  *G01N 33/548* (2006.01)
  *C07K 17/06* (2006.01)
  *C07D 403/12* (2006.01)
  *C07D 241/04* (2006.01)

(52) U.S. Cl. ............... 436/534; 436/529; 530/405; 530/406; 530/409; 530/410; 530/411; 544/360; 544/386

(58) Field of Classification Search ............... 530/405, 530/406, 409, 410, 411; 544/360, 386; 436/529, 436/534
See application file for complete search history.

(56) References Cited

U.S. PATENT DOCUMENTS 5,302,715 A  4/1994  Buechler et al.
5,413,999 A *  5/1995  Vacca et al. ............... 514/231.5

FOREIGN PATENT DOCUMENTS

| EP | 1207394 A2 | 2/2002 |
|---|---|---|
| FR | 2773994 | 7/1999 |
| WO | WO 95/23606 | 8/1995 |
| WO | WO 01/01135 A1 | 1/2001 |
| WO | WO 03/048386 | 6/2003 |
| WO | WO 03/075009 A1 | 9/2003 |

OTHER PUBLICATIONS

B. Dorsey et al, Journal of Medicinal Chemistry (1994), vol. 37, No. 21, pp. 3443-3451/.*

B. Dorsey et al, HCAPLUS accession No. 1995: 64944.*
J. Vacca et al, HCAPLUS accession No. 1995: 772577.*
Akeb, F. et al., "Quantification of plasma and intracellular levels of the HIV protease inhibitor ritonavir by competitive ELISA," Journal of Immunologial Methods 263 (2002) 1-9.
Eaglings, V.A. et al., "CPY3A4-mediated hepatic metabolism of the HIV-1 protease inhibitor saquinavir in vitro," Xenobiotica, 2002. vol. 31, No. 1, 1-17.
Mansfeld, H-W et al., "Detection of inhibition of HIV-1 protease activity by an enzyme-linked immunosorbent assay (ELISA)," Journal of Immunological Methods, 161 (1993) 151-155.
Marzolini, C. et al., "Simultaneous determination of the HIV protease inhibitors indinavir, amprenavir, saquinavir, ritonavir, nelfinavir and the non-nucleoside reverse transcriptase inhibitor efavirenz by high-performance liquid chromatography after solid-phase extraction,"0 Journal of Chromatography B, 740, (2000) 43-58.
Poirier, J-M et al., "Simultaneous Determination of the Five HIV-Protease Inhibitors: Amprenavir, Indinavir, Nelfinavir, Ritonavir, and Saquinavir in Human Plasma by Solid-Phase Extraction and Column Liquid Chromatography," Therapeutic Drug Monitoring, 22:465-473, 2000.
Remmel, R. et al., "Simultaneous HPLC Assay for Quantification of Indinavir, Nelfinavir, Ritonavir, and Saquinavir in Human Plasma," Clinical Chemistry, 46:1, 73-81 (2000).
Sarubbi, E. et al., "A high throughput assay for inhibitors of HIV-1 protease, Screening of microbial metabolites," FEBS 09419, vol. 279, No. 2, 265-269, (1991).
Valdez, H. et al., "Response to immunization with recall and neoantigens after prolonged administration of an HIV-1 protease inhibitor-containing regimen," AIDS, 2000, vol. 14, No. 1, 11-21.
Wiltshire, H.R. et al., "Chromatographic and Immunochemical Approaches to the Analysis of the HIV Protease Inhibitor Saquinavir in Plasma," Analytical Biochemistry, 281, 105-114 (2000).
Yu, S.-L. et al., "Assay of HIV-1 protease activity by use of crude preparations of enzyme and biotinlylated substrate," Journal of Virological Methods, 53 (1995) 63-73.

* cited by examiner

*Primary Examiner*—Mary E. Ceperley
(74) *Attorney, Agent, or Firm*—Marilyn L. Amick; Roche Diagnostics Operations, Inc.

(57) ABSTRACT

Derivatives and conjugates of indinavir for generation of antibodies and labeled conjugates for use for detection of indinavir in biological samples. The derivatives are synthesized out of the indane ring hydroxyl group or the pyridine ring nitrogen of indinavir. Also disclosed is synthesis of a major metabolite of indinavir (M6) in a single step from indinavir using palladium catalyst and hydrogen gas. Indinavir M6 has been extended to synthesize various analogs of indinavir with suitable functional groups. These derivatives are useful in the development of indinavir immunogens, antibodies, and labeled conjugates in the development of indinavir immunoassays.

28 Claims, 12 Drawing Sheets

US 7,202,092 B2

INDINAVIR DERIVATIVES USEFUL IN IMMUNOASSAY

RELATED APPLICATIONS

This application is a continuation-in-part of U.S. patent application Ser. No. 10/669,831 filed Sep. 24, 2003, now abandoned which is a continuation-in-part of U.S. patent application Ser. No. 10/192,052 filed Jul. 10, 2002, now abandoned which claims priority to U.S. Provisional Application No. 60/305,192 filed Jul. 13, 2001.

FIELD OF THE INVENTION

This invention relates to protease inhibitor derivatives useful in immunoassay. More specifically, this invention relates to activated indinavir haptens useful for generating immunogens and to conjugated derivatives useful as immunogens for producing antibodies to indinavir and in immunoassays for determination of indinavir in biological samples.

BACKGROUND OF THE INVENTION

HIV protease inhibitors are an important new class of drugs which have made a significant impact on the health care of AIDS patients since the first one, saquinavir, was introduced to the marketplace in 1995. Examples of other protease inhibitors include amprenavir, nelfinavir, lopinavir, ritonavir, indinavir, and atazanavir. They are especially effective in combination with other anti-HIV drugs such as reverse transcriptase inhibitors or with other HIV protease inhibitors. In spite of remarkable success with these new therapeutic regimens, there are strong indications that results would be much improved if therapeutic drug testing methods were available for monitoring the concentrations of protease inhibitors. Not all patients respond optimally to protease inhibitor combination therapies. Even those who do respond can subsequently develop drug resistance due to the notoriously high rate of mutation of the HIV virus. However, it has been shown that there is a clear relationship between plasma levels of the protease inhibitors and therapeutic efficacy based upon decreased viral load and increased CD4 cell count. One problem lies in the fact that the drugs are metabolized extensively and are subject to complex drug-drug interactions. The results are extremely complex pharmacokinetics and a strong element of unpredictability between dosage and resultant drug levels at any particular time for any particular patient. With therapeutic drug monitoring, drug dosages could be individualized to the patient, and the chances of keeping the virus in check would be much higher. But routine therapeutic drug monitoring of protease inhibitors would require the availability of simple automated tests adaptable to high throughput clinical analyzers. Currently most reports on therapeutic drug monitoring of protease inhibitors have used HPLC methods which are slow, labor-intensive, and expensive. Recently there was a report of a radioimmunoassay (RIA) method for saquinavir (Wiltshire et al., Analytical Biochemistry 281, 105–114, 2000). However, such a method would not be adaptable to high-throughput therapeutic drug monitoring and, like all RIA methods, suffers from the disadvantages of having regulatory, safety and waste disposal issues related to the radioactive isotope label used in the assay. The most desirable assay formats for therapeutic drug monitoring are non-isotopic immunoassays, and such methods have heretofore been unknown for monitoring HIV protease inhibitors.

Indinavir (CRIXIVAN, Merck & Co., Inc.) is one of the potent and specific inhibitors of human immunodeficiency virus protease. Indinavir is metabolized to low levels of quaternary pyridine N-glucuronide (M1), 2',3'-trans-dihydroxyindanylpyridine-N-oxide (M2), 2',3'-trans-dihydroxyindan (M3), and pyridine-N-oxide (M4a) analogs, and despyridylmethyl analogs of M3 (M5) and indinavir (M6). M6 is one of the major metabolites in urine as well as in plasma (Drug Metabolism and Disposition 24, 1389–94, 1996).

As previously mentioned, HPLC has been the method of choice for monitoring HIV protease inhibitors. Two recent reports in the literature describe HPLC assays for the simultaneous determination of several protease inhibitors in human plasma, Poirier et al., Therapeutic Drug Monitoring 22, 465–473, 2000 and Remmel et al., Clinical Chemistry 46, 73–81, 2000.

Chemical and biological assays generally involve contacting the analyte of interest with a pre-determined amount of one or more assay reagents, measuring one or more properties of a resulting product (the detection product), and correlating the measured value with the amount of analyte present in the original sample, typically by using a relationship determined from standard or calibration samples containing known amounts of the analyte of interest in the range expected for the sample to be tested. Typically, the detection product incorporates one or more detectable labels which are provided by one or more assay reagents. Examples of commonly used labels include functionalized microparticles, radioactive isotope labels such as 125I and 32P, enzymes such as peroxidase and beta-galactosidase and enzyme substrate labels, fluorescent labels such as fluoresceins and rhodamines, electron-spin resonance labels such as nitroxide free radicals, immunoreactive labels such as antibodies and antigens, labels which are one member of a binding pair such as biotin-avidin and biotin-streptavidin, and electrochemiluminescent labels such as those containing a ruthenium bipyridyl moiety. Sandwich assays typically involve forming a complex in which the analyte of interest is sandwiched between one-assay reagent which is ultimately used for separation, e.g., antibody, antigen, or one member of a binding pair, and a second assay reagent which provides a detectable label. Competition assays typically involve a system in which both the analyte of interest and an analog of the analyte compete for a binding site on another reagent, e.g., an antibody, wherein one of the analyte, analog or binding reagent possesses a detectable label.

Copending U.S. patent application Ser. No. 09/712,525 filed Nov. 14, 2000 having the same assignee as the present application and published as EP 1 207 394 on May 22, 2002, describes a non-isotopic immunoassay for an HIV protease inhibitor comprising incubating a sample containing the inhibitor with a receptor specific for the inhibitor or for a metabolite of said inhibitor and further with a conjugate comprising an analog of the inhibitor and a non-isotopic signal generating moiety. Signal generated as a result of binding of the inhibitor by the receptor is measured and correlated with the presence or amount of protease inhibitor in the original sample. The protease inhibitor conjugates of the present invention are especially useful in such an assay.

Copending U.S. patent application Ser. No. 10/192,052 filed Jul. 10, 2002 having the same assignee as the present application and published as WO 03/006506 on Jan. 23, 2003, describes activated haptens useful for generating immunogens to HIV protease inhibitors. Specifically disclosed are indinavir derivatives and immunogens synthesized out of the central hydroxyl group of the indinavir molecule.

There remains, among other problems, the need for improved activated haptens, derivatives, and conjugates of the HIV protease inhibitor indinavir and an immunoassay method for determination of indinavir in biological samples, the method suitable for automated, high-throughput drug monitoring. The present invention solves these and other problems.

SUMMARY OF THE INVENTION

It is against the above background that the present invention provides certain unobvious advantages and advancements over the prior art. In particular, the inventors have recognized a need for improvements in indinavir derivatives and conjugates useful in immunoassay.

The present invention relates to activated haptens useful for generating immunogens to the HIV protease inhibitor indinavir, to immunogens useful for generating antibodies to indinavir, and to labeled conjugates useful in immunoassays for determination of indinavir in biological samples. These compounds are synthesized out of the indane ring hydroxyl group of the pyridine ring nitrogen of indinavir and out of the pyridine nitrogen of indinavir. The invention also relates to a method for synthesizing the indinavir metabolite M6 in one step from indinavir in the presence of hydrogen gas and palladium catalyst and to activated haptens and conjugates derived from the indinavir M6 metabolite.

In one embodiment of the present invention, activated haptens are provided having the structure:

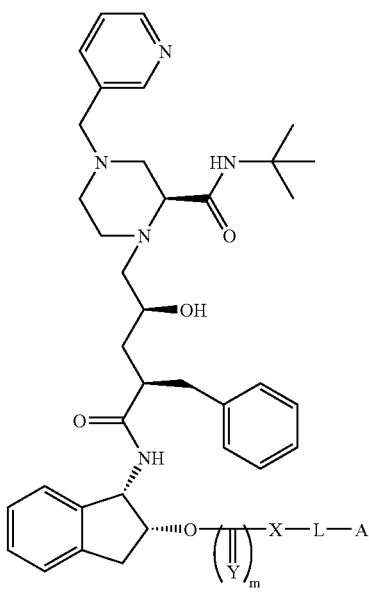

I where Y=O or S, m=0 or 1, X=CH$_2$ or NH, L is a linking group comprising 0 to 40 carbon atoms arrange straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

In another embodiment of the present invention, conjugated derivatives are provided having the structure:

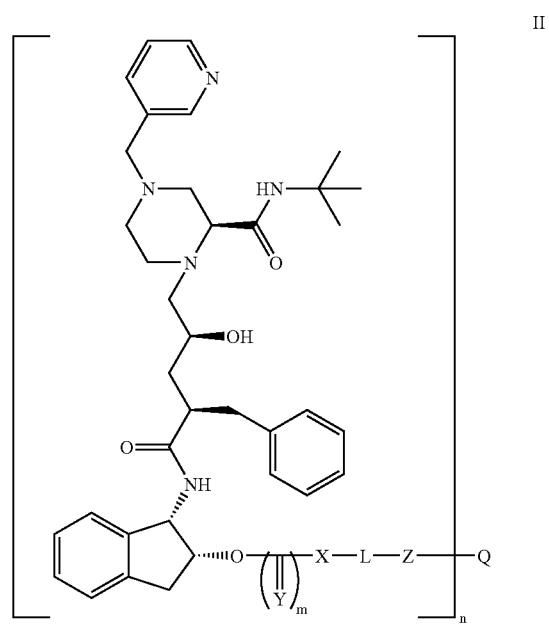

II where Y=O or S, m=0 or 1, X=CH$_2$ or NH, L is a linking group comprising 0 to 40 carbon atoms arrange straight or a branched chain, saturated or unsaturated, and further comprising up to two ring structures and 0–20 heteroatoms, with the proviso that not more than two heteroatoms may be linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

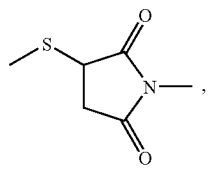

Q is selected from the group consisting of polypeptides, polysaccharides, synthetic polymers, and non-isotopic labels, and n is a number from 1 to 50 per 50 kilodaltons molecular weight of Q.

In another embodiment of the present invention, activated haptens are provided having the structure:

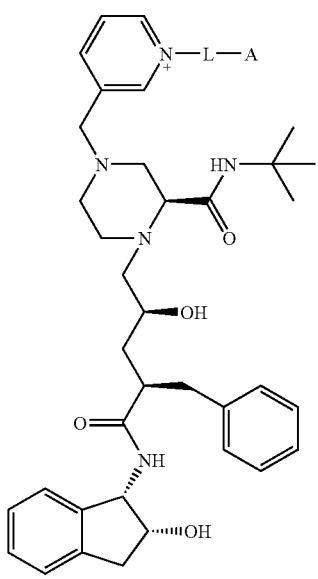

where L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

In another embodiment of the present invention, conjugated derivatives are provided having the structure:

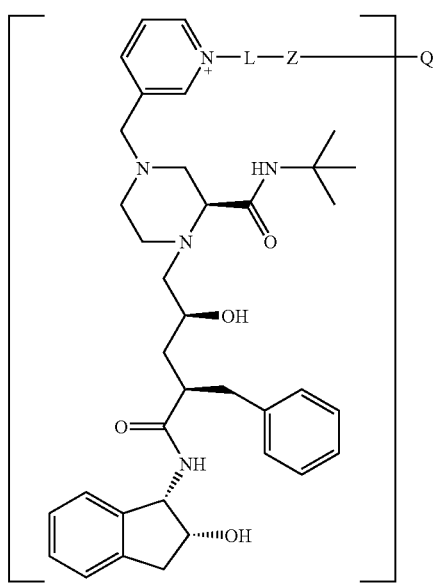

where L is a linking group comprising 0 to 40 carbon atoms arranged in a straight or a branched chain, saturated or unsaturated, and further comprising up to two ring structures and 0–20 heteroatoms, with the proviso that not more than two heteroatoms may be linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

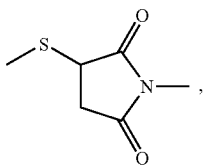

Q is selected from the group consisting of polypeptides, polysaccharides, synthetic polymers, and non-isotopic labels, and n is a number from 1 to 50 per 50 kilodaltons molecular weight of Q.

In yet another embodiment of the present invention, activated haptens are provided having the structure:

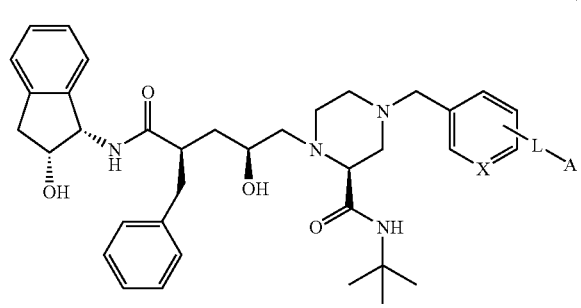

where X is N or C, L is a linking group comprising 0 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

In yet another embodiment of the present invention, conjugated derivatives are provided having the structure:

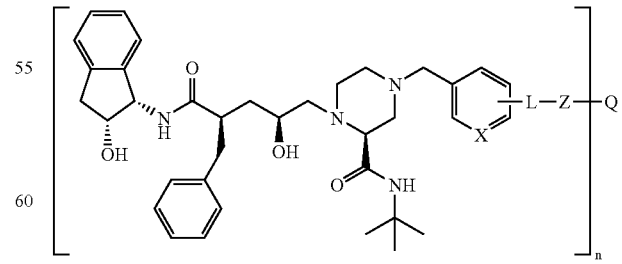

where X is N or C, L is a linking group comprising 0 to 40 carbon atoms arranged in a straight or a branched chain, saturated or unsaturated, and further comprising up to two ring structures and 0–20 heteroatoms, with the proviso that not more than two heteroatoms may be linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

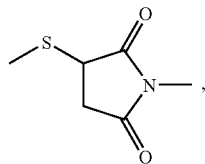

Q is selected from the group consisting of polypeptides, polysaccharides, synthetic polymers, and non-isotopic labels, and n is a number from 1 to 50 per 50 kilodaltons molecular weight of Q.

In a further embodiment of the present invention, activated haptens are provided having the structure:

VII

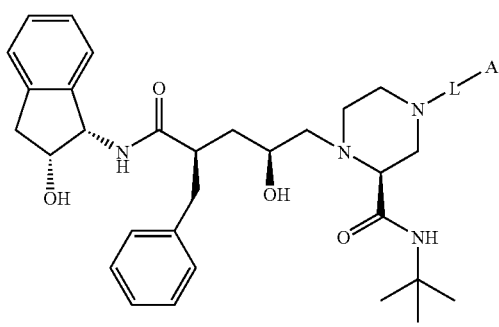

where L is an aliphatic linking group comprising 0 to 40 carbon atoms arranged in a straight or a branched chain, saturated or unsaturated, and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

In a further embodiment of the present invention, conjugated derivatives are provided having the structure:

VIII

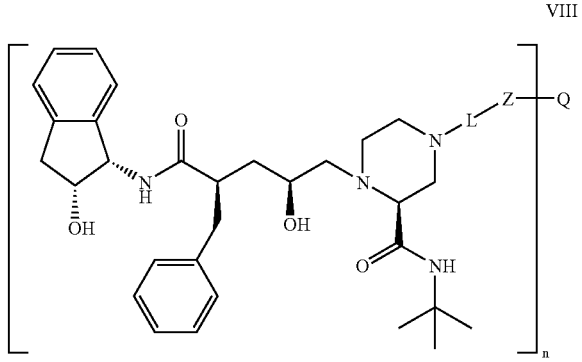

where L is an aliphatic linking group comprising 0 to 40 carbon atoms arranged in a straight or a branched chain, saturated or unsaturated, and further comprising 0–20 heteroatoms, with the proviso that not more than two heteroatoms may be linked in sequence, Z is a moiety selected from the group consisting of —CONH—, —NHCO—, —NH-CONH—, —NHCSNH—, —OCONH—, —NHOCO—, —S—, —NH(C=NH)—, —N=N—, —NH—, and

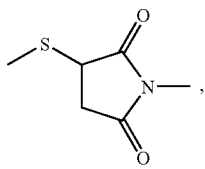

Q is selected from the group consisting of polypeptides, polysaccharides, synthetic polymers, and non-isotopic labels, and n is a number from 1 to 50 per 50 kilodaltons molecular weight of Q.

In another embodiment of the present invention, a method is provided for synthesizing the indinavir metabolite M6 in one step from indinavir in the presence of hydrogen gas and palladium catalyst. The synthetic M6 is useful in synthesis of indinavir derivatives having linking groups out of the piperazine nitrogen of M6. These linking groups include aliphatic, substituted aromatic, and pyridyl groups.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings.

DETAILED DESCRIPTION OF THE INVENTION

Figure 1:
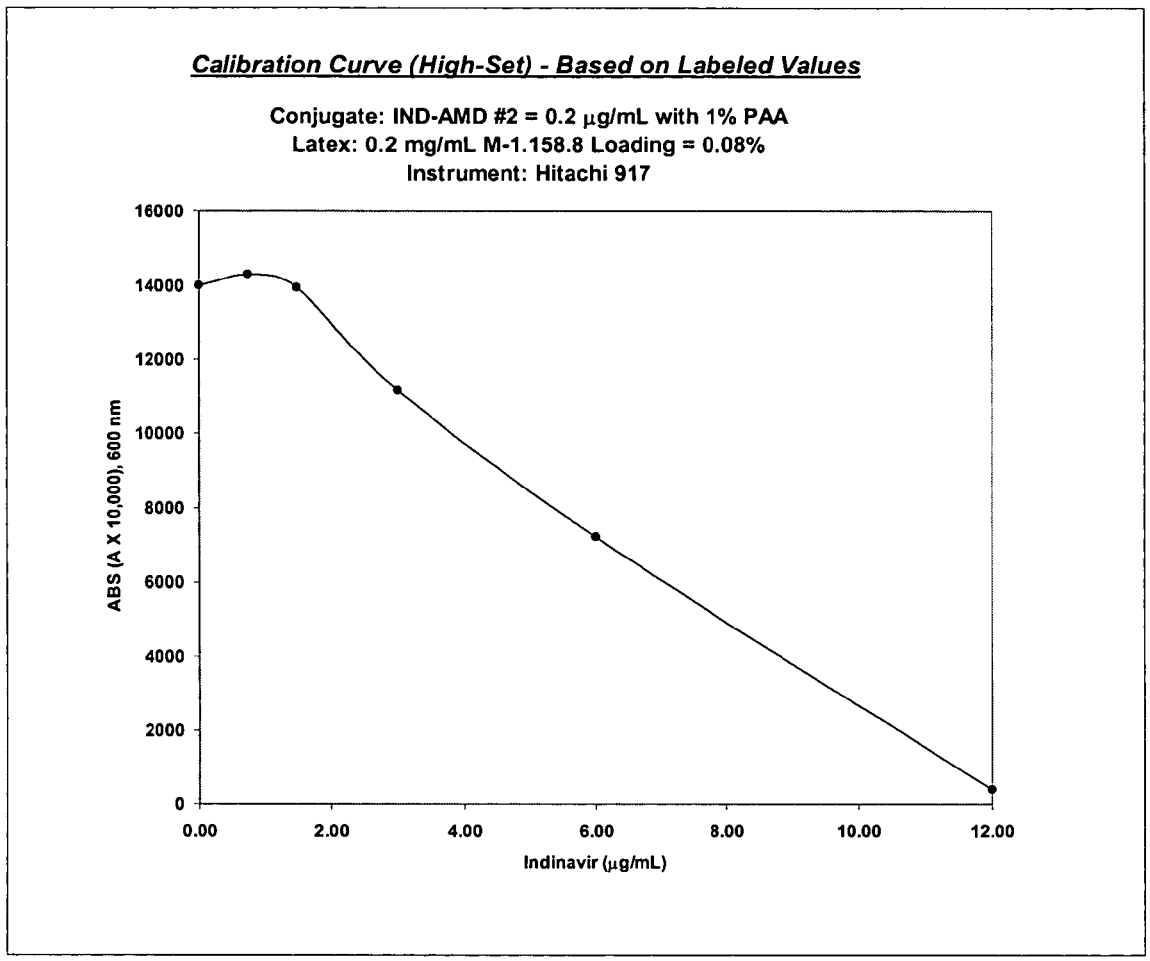
FIG. 1 is a calibration curve prepared using conjugate 6C using high-set serum calibrators as described in Example 29.
Figure 2:
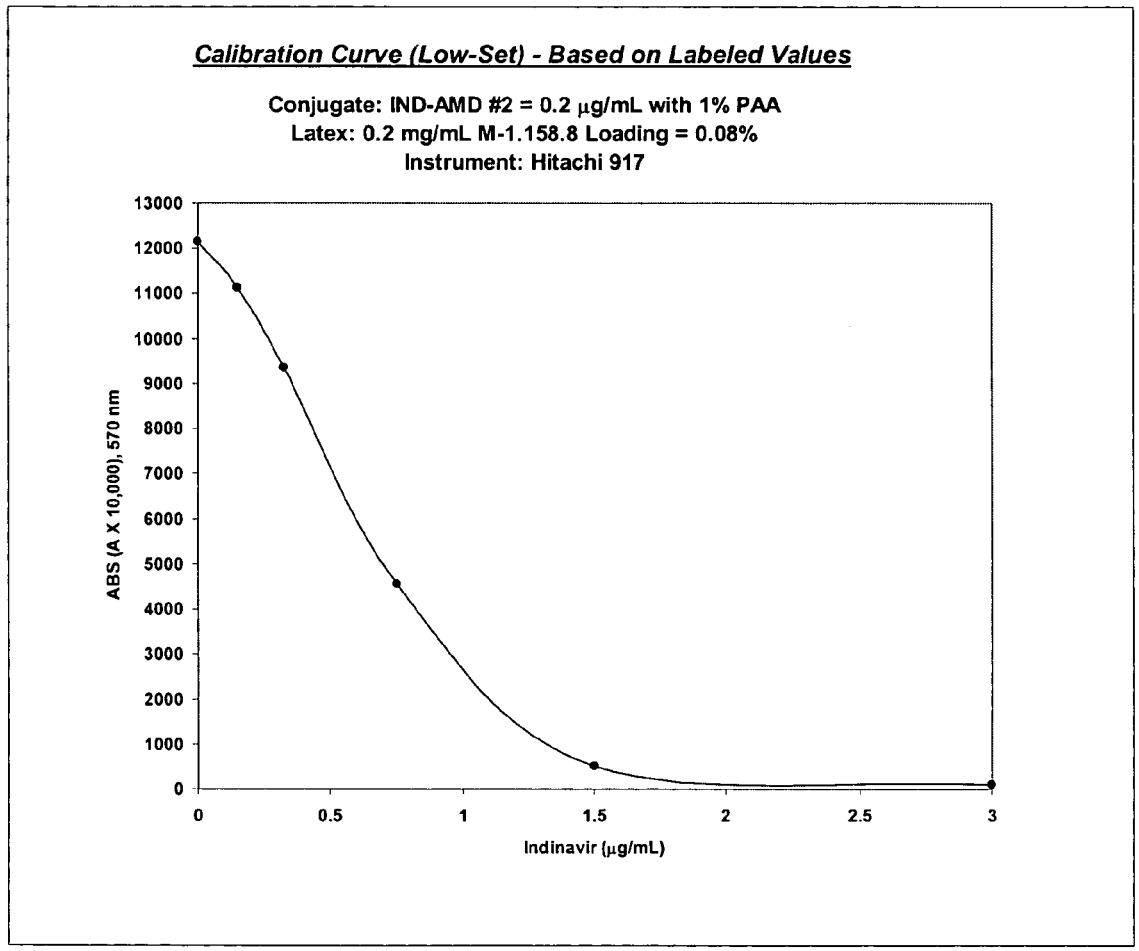
FIG. 2 is a calibration curve prepared using conjugate 6C using low-set serum calibrators as described in Example 29.
Figure 3:
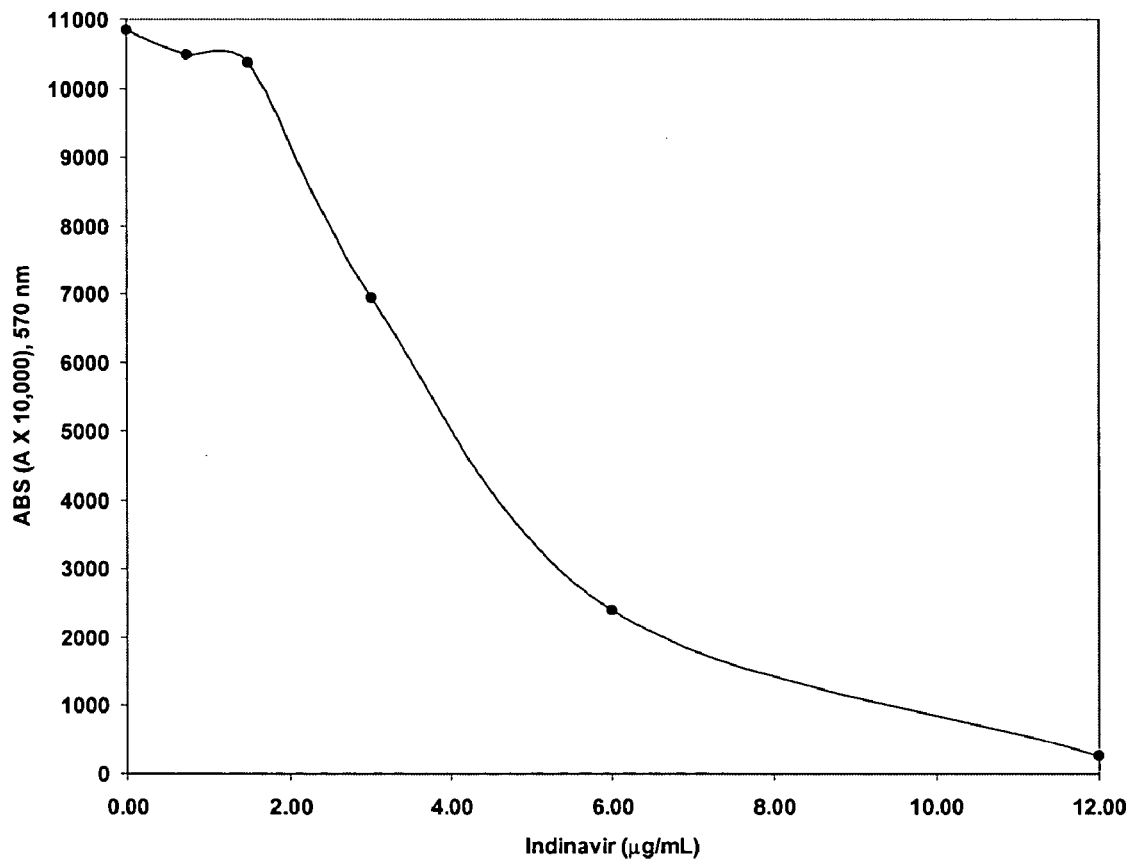
FIG. 3 is a calibration curve prepared using conjugate 13C using high-set serum calibrators as described in Example 29.
Figure 4:
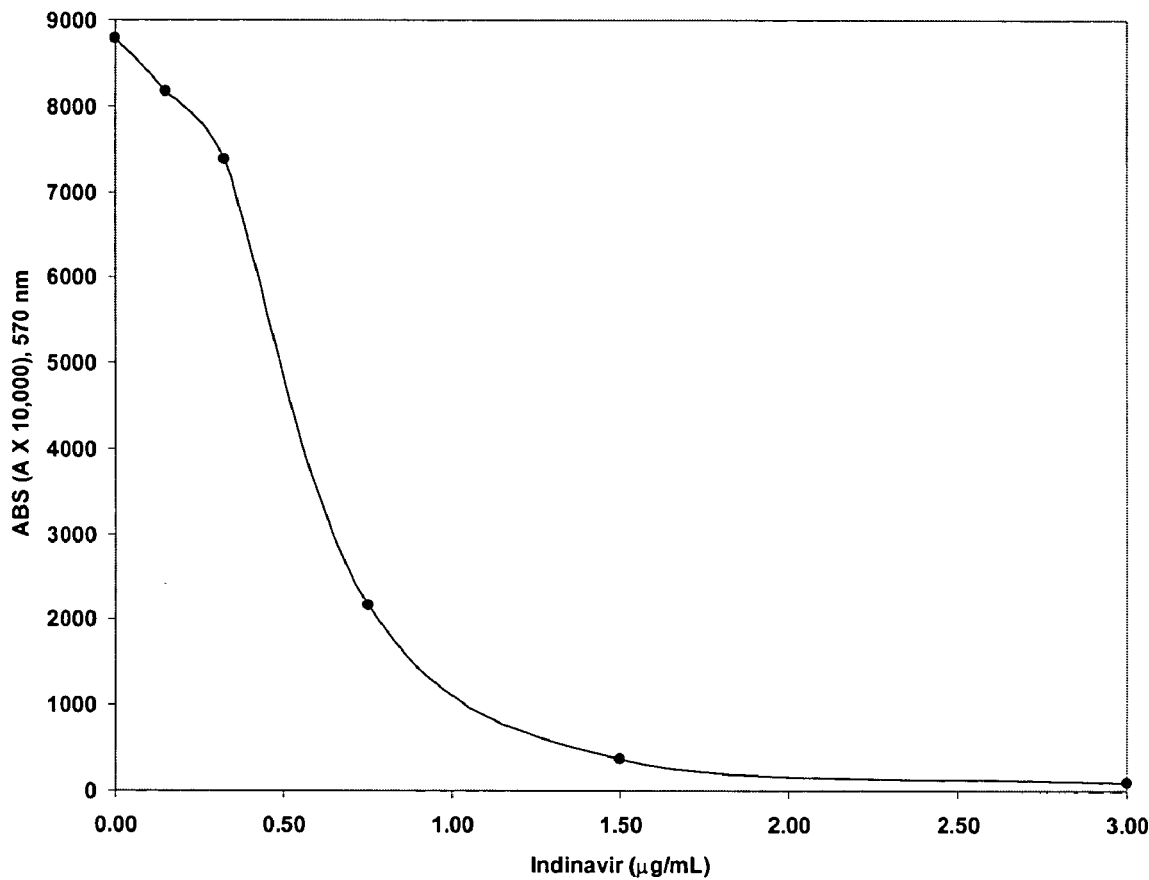
FIG. 4 is a calibration curve prepared using conjugate 13C using low-set serum calibrators as described in Example 29.

In order that the invention may be more readily understood, reference is made to the following examples, which are intended to illustrate the invention, but not limit the scope thereof.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

Throughout the specification, numbers in boldface type are used refer to chemical structures illustrated in the drawings.

As used herein, analyte refers to a substance, or group of substances, whose presence or amount thereof is to be determined.

Antibody means a specific binding partner of the analyte and is any substance, or group of substances, which has a specific binding affinity for the analyte to the essential exclusion of other unrelated substances. The term includes polyclonal antibodies, monoclonal antibodies, and antibody fragments.

Haptens are partial or incomplete antigens. They are protein-free substances, mostly low molecular weight substances, which are not capable of stimulating antibody formation, but which do react with antibodies. The latter are formed by coupling a hapten to a high molecular weight carrier and injecting this coupled product into humans or animals. Examples of haptens include therapeutic drugs such as digoxin, and theophylline, protease inhibitors such as saquinavir and indinavir, drugs of abuse such as morphine and LSD, antibiotics such as gentamicin and vancomycin, hormones such as estrogen and progesterone, vitamins such as vitamin B12 and folic acid, thyroxin, histamine, serotonin, adrenaline and others.

An activated hapten refers to a hapten derivative that has been provided with an available site for reaction, such as by the attachment of, or furnishing of, an activated group for synthesizing a derivative conjugate.

The term linker refers to a chemical moiety that connects a hapten to a carrier, immunogen, label, tracer or another linker. Linkers may be straight or branched, saturated or unsaturated carbon chains. They may also include one or more heteroatoms within the chain or at termini of the chains. By heteroatoms is meant atoms other than carbon which are chosen from the group consisting of oxygen, nitrogen and sulfur. The use of a linker may or may not be advantageous or needed, depending on the specific hapten and carrier pairs.

A carrier, as the term is used herein, is an immunogenic substance, commonly a protein, which can join with a hapten, thereby enabling the hapten to stimulate an immune response. Carrier substances include proteins, glycoproteins, complex polysaccharides and nucleic acids that are recognized as foreign and thereby elicit an immunologic response from the host.

The terms immunogen and immunogenic as used herein refer to substances capable of producing or generating an immune response in an organism.

The terms conjugate and derivative refer to a chemical compound or molecule made from a parent compound or molecule by one or more chemical reactions.

As used herein, a detector molecule, label or tracer is an identifying tag which, when attached to a carrier substance or molecule, can be used to detect an analyte. A label may be attached to its carrier substance directly or indirectly by means of a linking or bridging moiety. Examples of labels include enzymes such as β-galactosidase and peroxidase, fluorescent compounds such as rhodamine and fluorescein isothiocyanate (FITC), luminescent compounds such as dioxetanes and luciferin, and radioactive isotopes such as 125I.

The term active ester within the sense of the present invention encompasses activated ester groups which can react with nucleophiles such as, but not limited to, free amino groups of peptides, polyaminoacids, polysaccharides or labels under such conditions that no interfering side reactions with other reactive groups of the nucleophile-carrying substance can usefully occur.

The following structure illustrates various positions for derivatization referred to herein, wherein X=CH$_2$ or N:

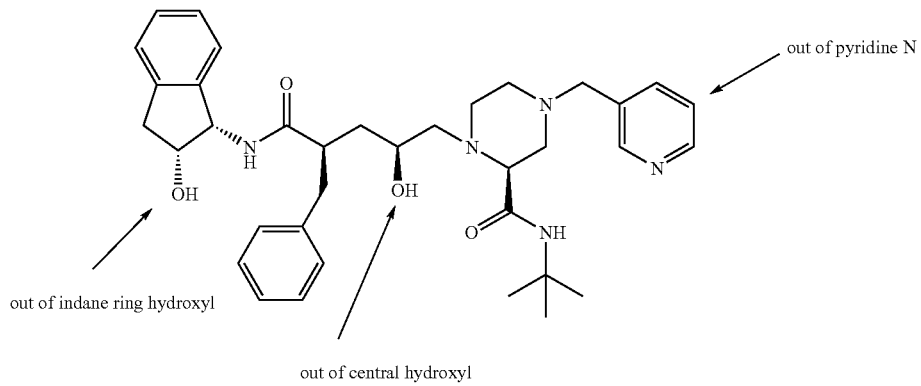

out of indane ring hydroxyl out of central hydroxyl out of pyridine N

Indinavir derivatives and conjugates synthesized out of the central hydroxyl group of the indinavir molecule are described in WO 03/006506.

One embodiment of the present invention relates to indinavir hapten structures leashed out of pyridine nitrogen of indinavir.

Figure 7:
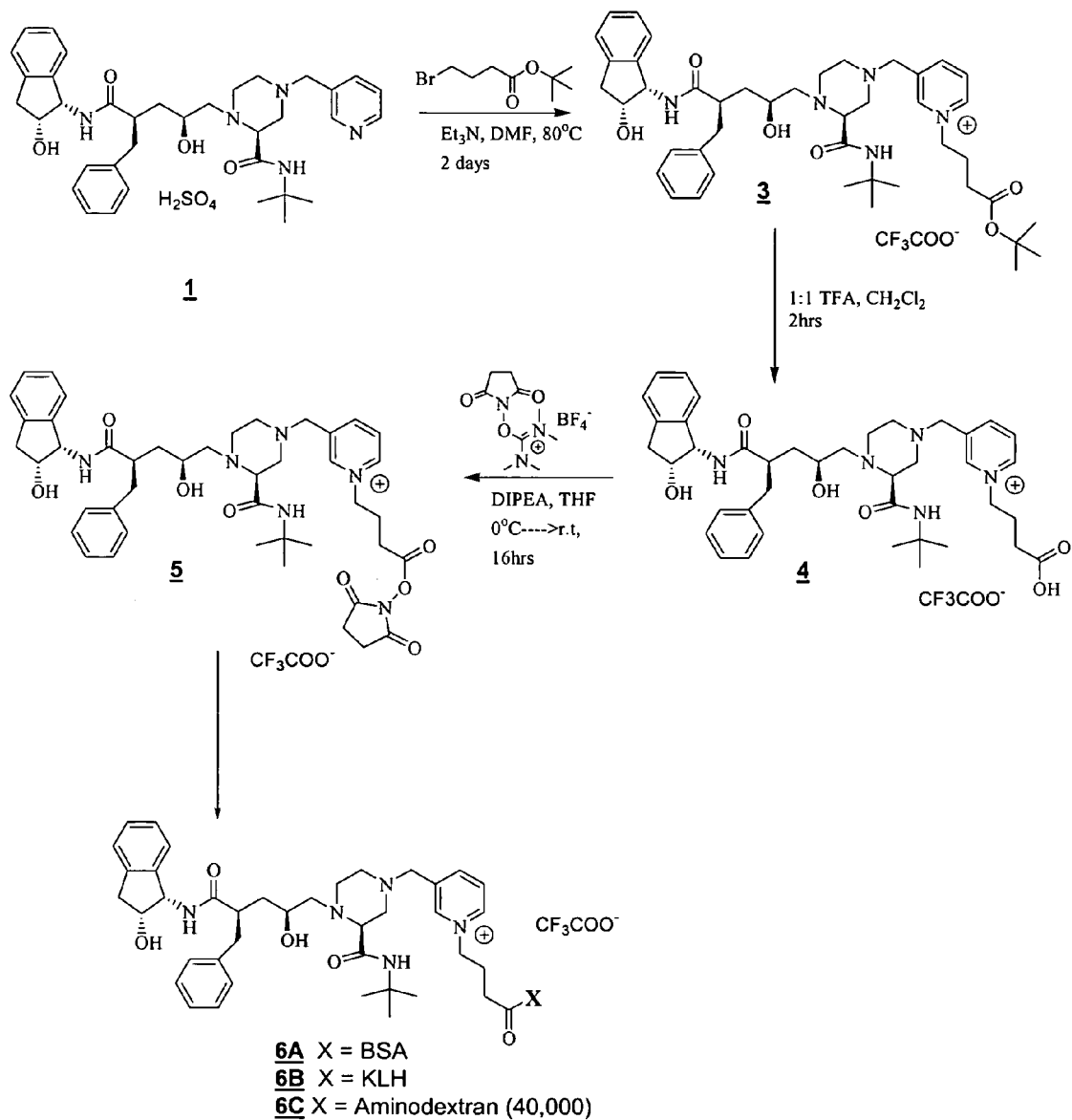
FIG. 7 illustrates a scheme for synthesis of the activated indinavir hapten 5 out of the pyridine ring nitrogen of indinavir as described in Examples 9–11 and the KLH, BSA, and aminodextran derivatives as described in Examples 12, 13, and 27, respectively.

Adjustment of reaction conditions allows for selection of one reaction site over another. An example of this approach involves an alkylation reaction of indinavir sulfate in the presence of a tertiary amine, preferably triethylamine. Such alkylation reactions selectively functionalize the indinavir pyridine nitrogen as shown in FIG. 7:

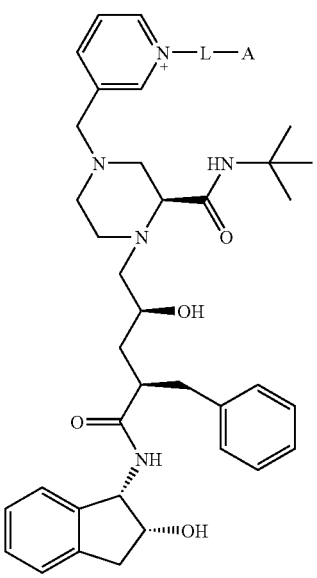

III where L is a linking group comprising 0 to 40 carbon atoms arranged in a straight chain or a branched chain, saturated or unsaturated, and containing up to two ring structures and 0–20 heteroatoms, with the proviso that not more than two heteroatoms may be linked in sequence. A is an activated functionality selected from the group consisting of active esters, isocyanates, isothiocyanates, thiols, imidoesters, anhydrides, maleimides, and thiolactones.

The alkylating reagents are preferably a halo alkylating agent bearing a protected carboxylic acid or appropriately protected functionality such as an amino group protected as the phthalimide group. The protected carboxyl group is preferably an ester which is removed under acidic or basic conditions after being attached to indinavir, for example, compound 4 in FIG. 7. The free carboxylic acid group may be activated to give an active ester for subsequent conjugation to polypeptides, polysaccharides, and labeling groups. The free amino group, after deprotection, can also be extended using a bi-functional linker with an activated carboxylic acid group, or it can be coupled to a polypeptide by means of a urea linkage or similar group.

Linker extension can also be accomplished with heterobifunctional reagents such as maleimido alkanoic acid N-hydroxysuccinimide esters to generate terminal maleimido groups for subsequent conjugation to thiol groups on polypeptides and labels. Alternatively, an amino-terminated linker can be extended with a heterobifunctional thiolating agent that reacts to form an amide bond at one end and a free or protected thiol at the other end. Some examples of thiolating reagents of this type which are well-known in the art are 2-iminothiolane (2-IT), succinimidyl acetylthiopropionate (SATP) and succinimido 2-pyridyldithiopropionate (SPDP). The incipient thiol group is then available, after deprotection, to form thiol ethers with maleimido or bromoacetylated modified immunogens or labels.

Active esters of this invention are reactive with nucleophiles, especially primary amines, at relatively low temperatures, in a variety of aqueous and non-aqueous solvent mixtures. Typical conditions for active ester couplings with primary or secondary amines to give amides are reaction in dipolar aprotic solvents such as N,N-dimethylformamide (DMF) or dimethylsulfoxide (DMSO) with or without added water at room temperature.

A buffer or a tertiary amine is often added to maintain the basic pH needed to keep the primary amine reactant in a deprotonated state. Common active esters are p-nitrophenylesters, N-hydroxysulfosuccimidyl esters, N-hydroxysuccimidyl esters, 1-hydroxybenzotriazolyl esters and pentafluorophenyl esters. The preferred active ester is N-hydroxysuccinimide esters because of their balance of stability, reactivity and the easy removal of side product N-hydroxysuccinimide. Other active esters are well known to those skilled in the art and may be used similarly.

Alternatively, indinavir derivatives with linkers bearing an ester; or iminium group as the activated group may be obtained by, for example, using a linker carrying a suitable precursor group, for example, a terminal nitrile group. As example, an indinavir derivative, carrying a terminal nitrile may be synthesized in a manner analogous to that described above, followed by conversion of the nitrile to an imidate moiety (imido imidate group by methods known in the art, for example, by treatment with hydrogen chloride in an alcohol. See also: Hermanson, ibid; and Jerry March, Advanced Organic Chemistry, 3rd Ed., John Wiley & Sons, 1985. Other methods of obtaining imido esters will be suggested to one skilled in the art.

Another embodiment of the present invention relates to indinavir derivatives leashed out of the indane hydroxyl group. These activated haptens have the structure:

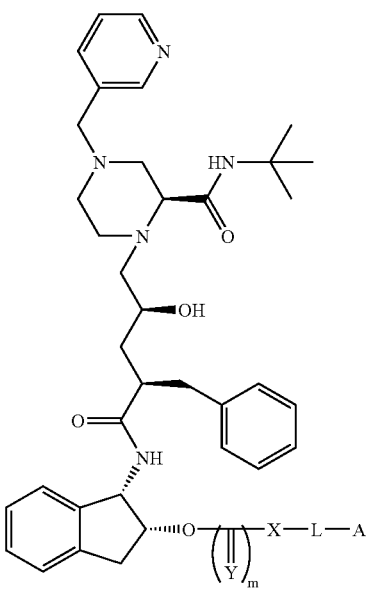

I wherein Y is O, S or NH, m is 0 or 1, L is a linking group comprising 0 to 40 carbon atoms arranged in a straight chain or a branched chain, saturated or unsaturated, and containing up to two ring structures and 0–20 heteroatoms, with the proviso that not more than two heteroatoms may be linked in sequence. A is an activated functionality selected from the group consisting of active esters, isocyanates, isothiocyanates, thiols, imidoesters, anhydrides, maleimides, thiolactones, and aldehydes.

Indinavir contains two secondary hydroxyl groups, the indane hydroxyl and the central hydroxyl, and it may be necessary initially to protect the hydroxyl group of the indane ring. Selective modification requires protection of hydroxyl group of the indane ring bridging to the adjacent amide nitrogen of indinavir using the isopropylidine ring system, following protection of the central hydroxyl group of indinavir. Many suitable protecting groups are well known in the art. See, for example, "Protective Groups in Organic Synthesis, 2nd edition, T. Greene and P. Wuts, Wiley-Interscience, 1991.

Figure 5:
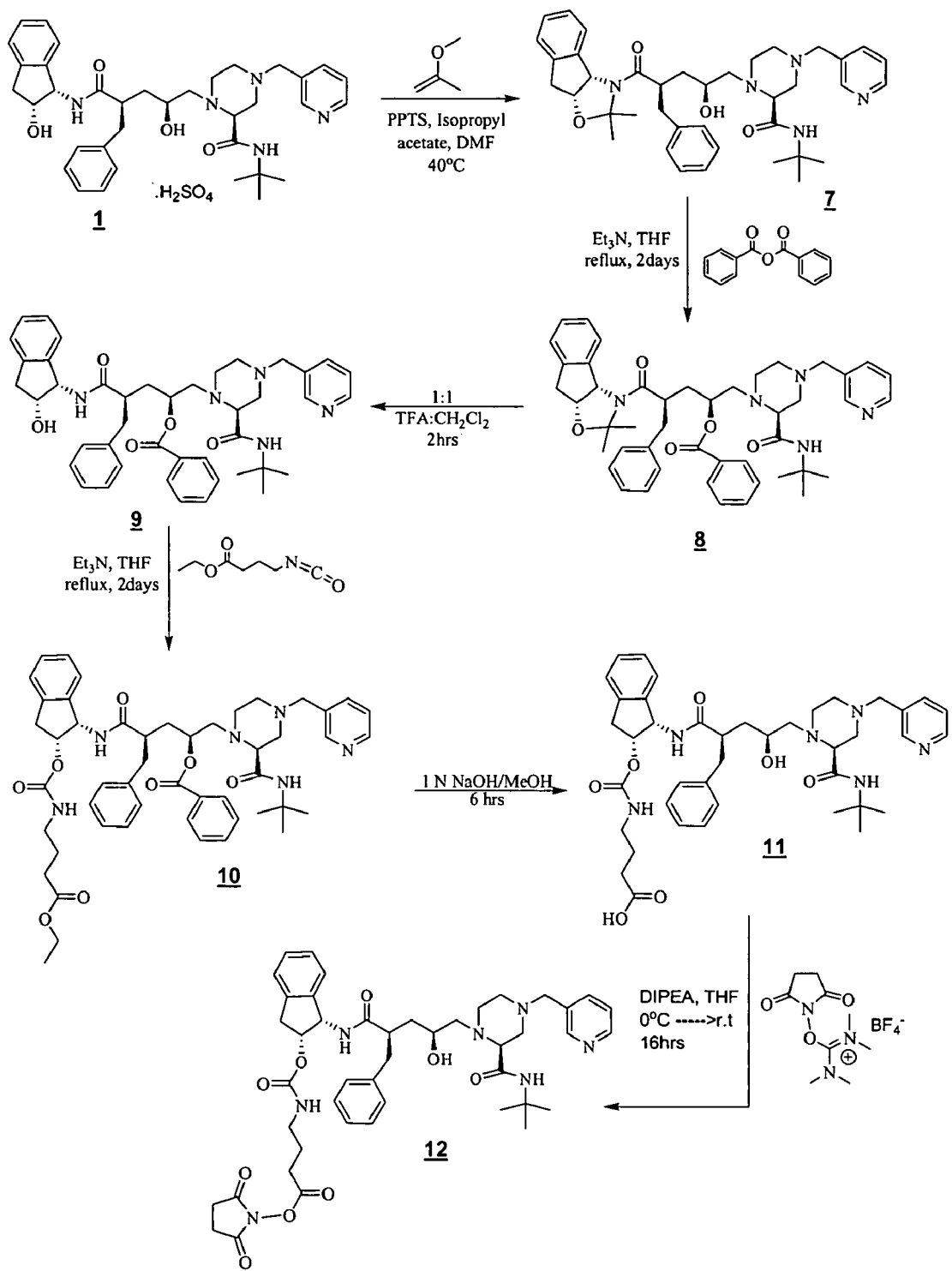
FIG. 5 illustrates a scheme for synthesis of the activated indinavir hapten 12 out of the indane ring hydroxyl group of indinavir as described in Examples 1–6.

The central hydroxyl group can be protected as a silyl protecting group, e.g., a TBDMS (t-butyldimethylsilyl) or TBDPS (t-butyldiphenylsilyl) group. An ester group can also be used to protect the central hydroxy functionality of isopropylidine protected indinavir, preferably a benzoate group in the presence of a base, expecially triethylamine. See compound 8 in Example 2 and in FIG. 5. The protection of the central hydroxyl group through an acylation reaction is carried out in a suitable solvent such as DMF, preferably THF, for a time which typically ranges from 0.5 hours to 7 days. Following deprotection of the isopropylidine group, the indane hydroxyl group can be modified to give a urethane bond at the point of attachment. The indane hydroxyl can also be modified to give an ether bond at the point of attachment while the central hydroxyl group of indinavir is protected as a silyl group. For example, the isopropylidine group of indinavir derivative with a TBDMS protected at the central hydroxyl position can be deprotected under acidic conditions, and the released indane hydroxyl group may be subjected to alkylation conditions using halo alkylating agents bearing a protected carboxylic acid or appropriately protected functionality such as an amino group protected as phthalimide to form ether linkages. A carboxyalkylisocyanate with or without a protecting group on the carboxyl group may be reacted directly with the target hydroxyl group of indinavir to give a protected carboxylurethane or a carboxyarylurethane. The protected carboxyl group is preferably an ester which is removed under basic or acidic conditions. The carboxyl group may be converted to an active ester for subsequent conjugation or may be directly conjugated to polypeptides, polysaccharides, and labels. Alternatively, a preactivated carboxyalkylisocyanate or carboxyarylisocyanate such as N-hydroxysuccinimidyl isocyanatobenzoate may be reacted directly with indinavir hydroxyl groups.

Alternative carboxylic acid activation is through anhydride formation. In general, carboxylic acids are reacted with alkylchloroformates such as isobutylchloroformate at a temperature typically ranging from −30° C. to +30° C., usually −20° C. to 0° C., in the presence of a tertiary amine such as triethylamine or N-methylmorpholine in solvents such as DMF or THF. The mixed anhydride is then reacted with amino groups on labels, proteins or peptides to give stable amide conjugates.

Another activation method for a protease inhibitor linked with carboxylic acids is conversion to masked thiol groups, such as thiolactones, by coupling of the carboxylic acid group with a substance such as homocysteine thiolactone (U.S. Pat. No. 5,302,715). The resulting linker-thiolactone may then be unmasked with mild base to give a terminal thiol which is then reactive with moieties like maleimido groups or bromoacetyl groups or iodoacetyl groups, such as on maleimido- or haloacetyl-modified peptides, polysaccharides, polyaminoacids, and labels to give thio-maleimido or thiol-acetyl adducts.

Another embodiment of the present invention relates to a process for producing indinavir M6. This one-step reduction can be made under hydrogenation conditions using catalysts, e.g., 10% Pd-C, 5% Pd-C, ammonium formate/Pd-C, and 20% palladium hydroxide on C in a solvent such as methanol, ethanol, acetic acid, or THF, especially methanol at room temperature under pressure ranging from 1 atm to 60 psi.

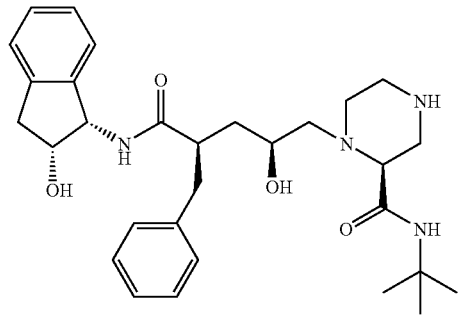

2

The resulting indinavir M6 can be used to prepare new indinavir hapten derivatives as described below.

In another embodiment of the present invention, the indinavir derivative is leashed out of the pyridine ring or benzene ring as represented by the formula:

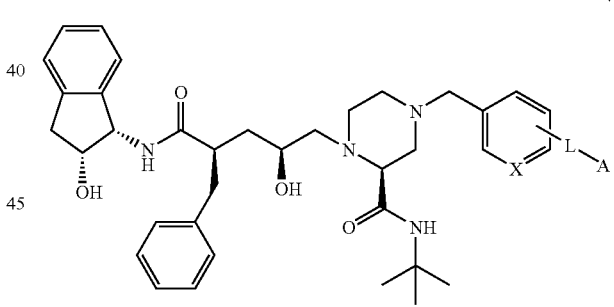

V wherein Y is O, S or NH, m is 0 or 1, L is a linking group consisting of 0 to 40 carbon atoms arranged in a straigh chain or a branched chain, saturated or unsaturated, and containing up to two ring structures and 0–20 heteroatoms, with the proviso that not more than two heteroatoms may be linked in sequence. A is an activated functionality chosen from the group consisting of active esters, isocyanates, isothiocyanates, thiols, imidoesters, anhydrides, and maleimides.

The properly functionalized and protected alkyl halo pyridine derivative can be coupled with indinavir M6 under basic conditions. The coupling reaction of the cyclic secondary amine group of the piperazine moiety of indinavir M6 and properly functionalized and protected formyl pyridine derivative can also be carried out under reductive amination conditions to give the same product.

Figure 10:
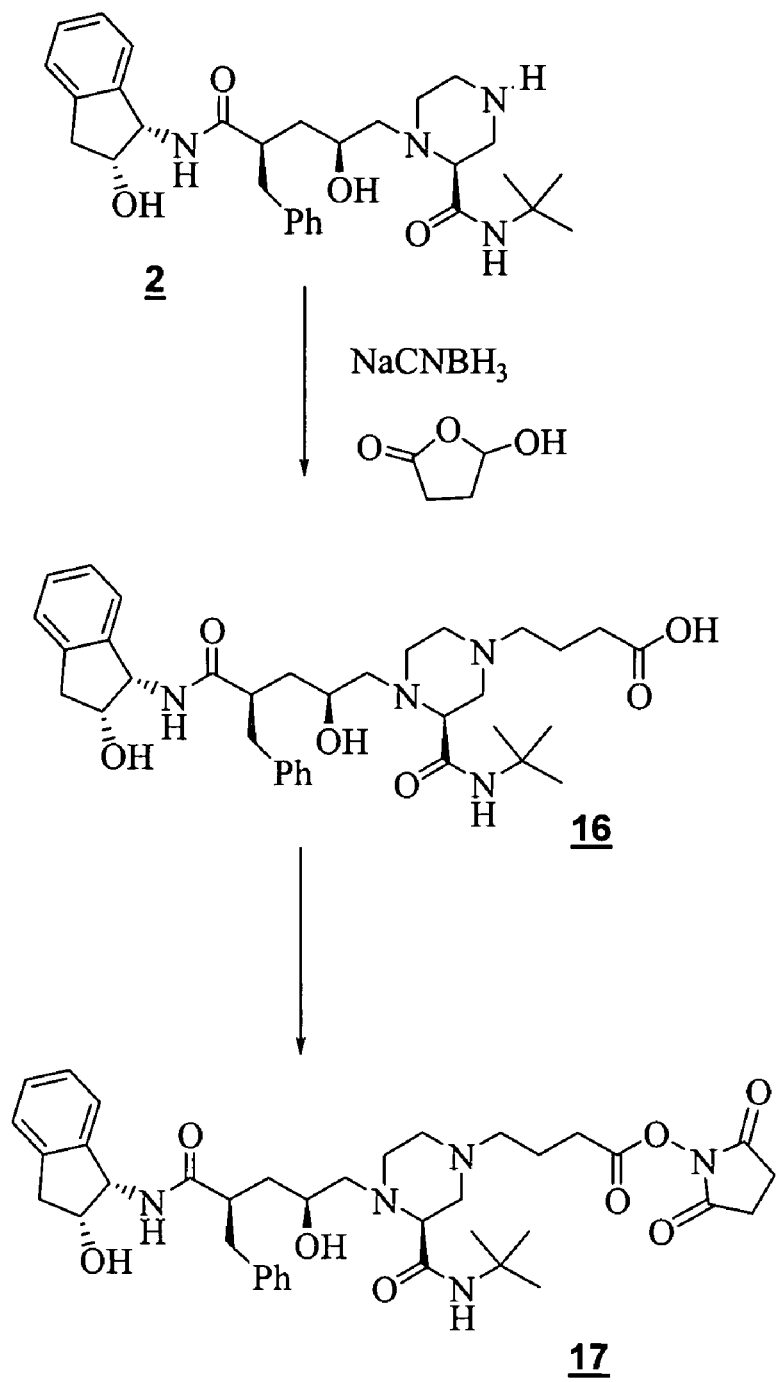
FIG. 10 illustrates a scheme for synthesis of indinavir derivatives having an aliphatic linking group out of the piperazine nitrogen of M6 as described in Examples 17 and 18.
Figure 12:
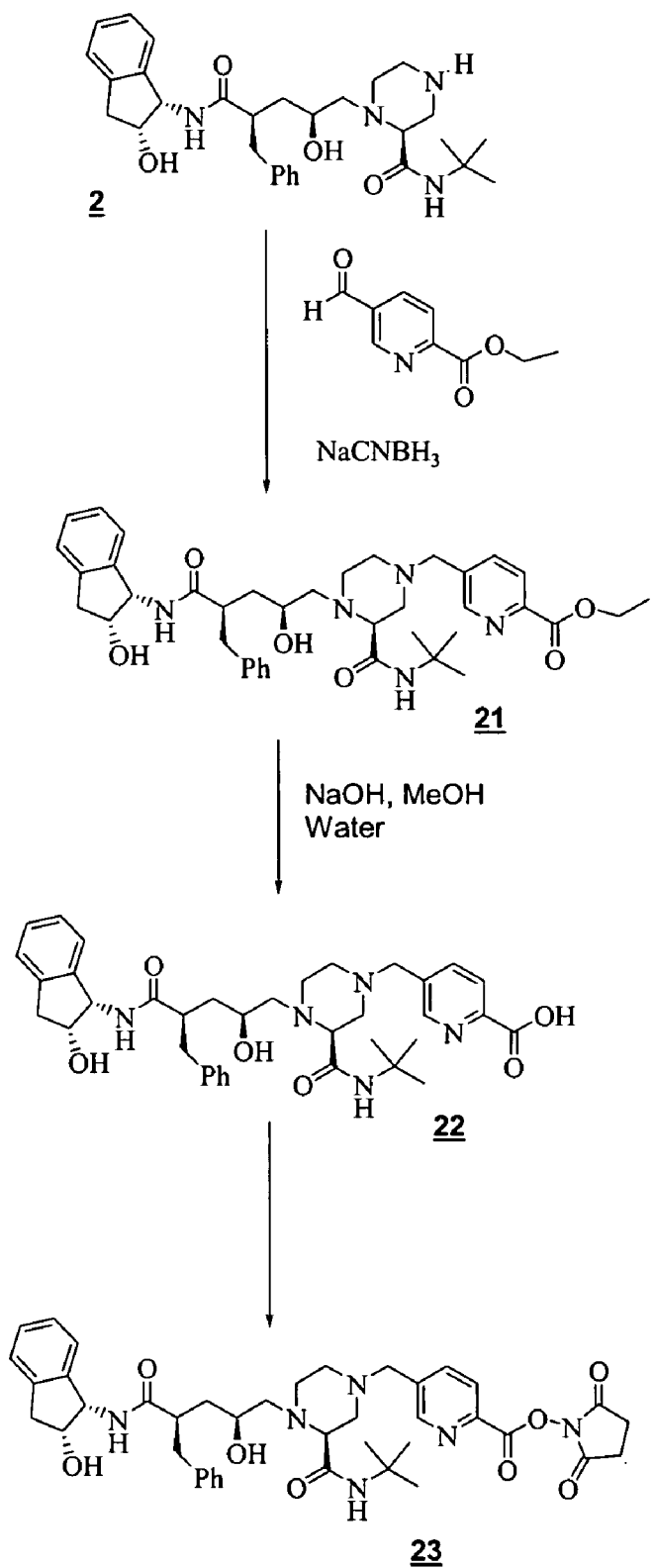
FIG. 12 illustrates a scheme for synthesis of indinavir derivatives having a pyridyl linking group out of the piperazine nitrogen of M6 as described in Examples 22–24.

Properly protected alkyl halo benzene derivative and aromatic aldehyde derivatives can also be used in a similar way to couple to indinavir M6 (see Example 21 and FIG. 12). Aliphatic linkers can also be attached to the piperazine moiety of indinavir M6 using similar chemistry as described above using properly functionalized aliphatic halo alkyl linkers under basic conditions or using properly functionalized aliphatic aldehyde or commercial succinic under reductive amination conditions. For example, compound 16 (FIG. 10) can be prepared using succinic semialdehyde in the presence of sodium cyanoborohydride.

These activated haptens have the structure:

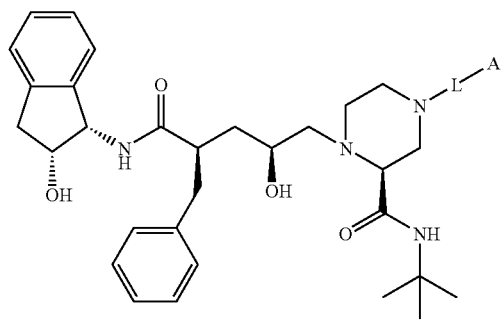

VII wherein Y is O, S or NH, m is 0 or 1, L is an aliphatic linking group consisting of 0 to 40 carbon atoms arranged in a straight chain or a branched chain, saturated or unsaturated, and 0–20 heteroatoms, with the proviso that not more than two heteroatoms may be linked in sequence. A is an activated functionality chosen from the group consisting of active esters, isocyanates, isothiocyanates, thiols, imidoesters, anhydrides and maleimides.

Another embodiment of the present invention relates immunogens having structures selected from the following:

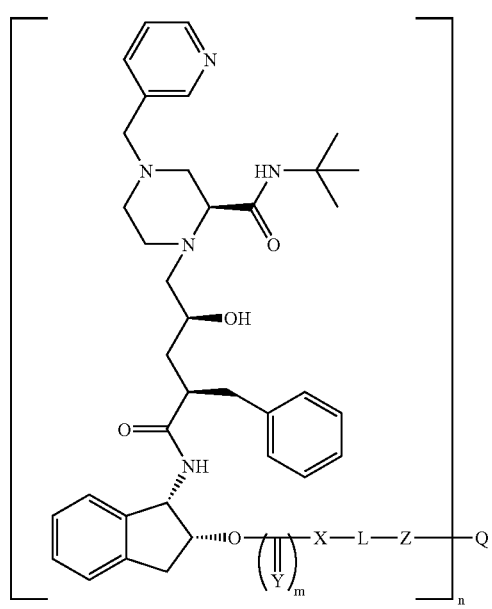

II

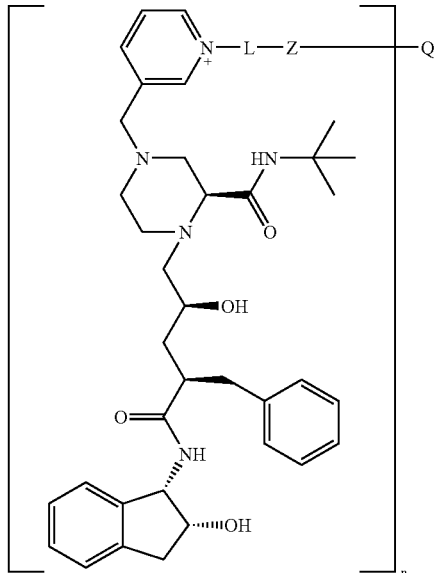

IV

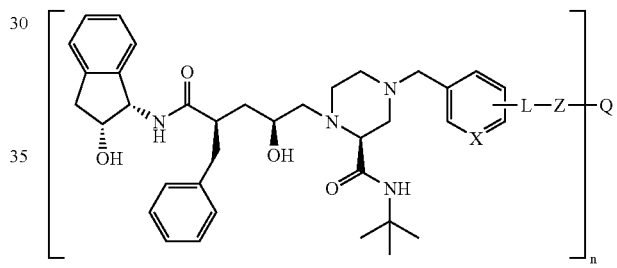

VI

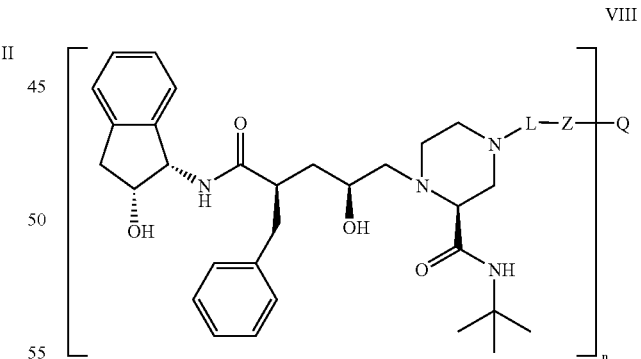

VIII where X is N or C, L is a linking group comprising 0 to 40 carbon atoms arranged in a straight or a branched chain, saturated or unsaturated, and further comprising up to two ring structures and 0–20 heteroatoms, with the proviso that not more than two heteroatoms may be linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

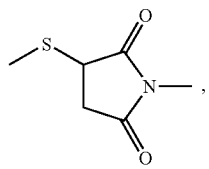

Q is selected from the group consisting of polypeptides, polysaccharides, synthetic polymers, and non-isotopic labels, and n is a number from 1 to 50 per 50 kilodaltons molecular weight of Q, with the further proviso that in structure VIII, L is an aliphatic linking group comprising 0 to 40 carbon atoms arranged in a straight or a branched chain, saturated or unsaturated, and further comprising 0–20 heteroatoms.

The immunogenic carrier is typically a polypeptide or a polysaccharide with a molecular weight greater than 10 kD. Examples of preferred carrier substances include keyhole limpet hemocyanin (KLH), limulus polyphemus hemocyanin (LPH), and bovine thyroglobulin (BTG). The reaction between the activated hapten derivative as described earlier and amino groups on the carrier is typically carried out in a buffered mixture of water and a water miscible organic solvent such as DMSO at room temperature for 0.5 to 5 days. The pH of the buffer is typically between 6 and 8 for active esters, isocyanates, and isothiocyanates, or between 7 and 10 for imidates, and is adjusted according to the known reactivity of the carrier amino groups and the activated functionality. In the case where the terminal group A is a maleimide, the reactive groups on the carrier are thiols. These thiol groups are either native to the carrier or may be introduced using thiolating reagents such as 2-IT or SATP. The optimum pH for the conjugation of maleimides to thiol groups to give thioethers is typically between 5 and 7. Following the reaction, the immunogen is dialyzed or subjected to size exclusion chromatography in order to remove unconjugated hapten and organic solvent.

An alternative method of obtaining immunogens is by reaction of an activated hapten wherein the activating group is aldehyde with the amino groups of a carrier protein or polypeptide to form a Schiff base, followed by reduction with mild reducing agents such as a cyanoborohydride, to form a stable amine bond. Variations on this last approach will also be suggested to those skilled in the art to which the present invention belongs.

In order to generate antibodies, the immunogen can be prepared for injection into a host animal by rehydrating lyophilized immunogen to form a solution or suspension of the immunogen. Alternatively, the immunogen may be used as a previously prepared liquid solution or as a suspension in buffer. The immunogen solution is then combined with an adjuvant such as Freund's to form an immunogen mixture. The immunogen may be administered in a variety of sites, at several doses, one or more times, over many weeks.

Preparation of polyclonal antibodies using the immunogens of the invention may follow any of the conventional techniques known to those skilled in the art. Commonly, a host animal such as a rabbit, goat, mouse, guinea pig, or horse is injected with the immunogen mixture. Further injections are made, with serum being assessed for antibody titer until it is determined that optimal titer has been reached. The host animal is then bled to yield a suitable volume of specific antiserum. Where desirable, purification steps may be taken to remove undesired material such as nonspecific antibodies before the antiserum is considered suitable for use in performing assays.

Monoclonal antibodies may be obtained by hybridizing mouse lymphocytes, from mice immunized as described above, and myeloma cells using a polyethylene glycol method such as the technique described in *Methods in Enzymology* 73 (Part B), pp. 3–46, 1981.

In the case of ELISA assays, indinavir derivatives coupled to bovine serum albumin (BSA) are preferred for coating of microtiter plates.

For the synthesis of conjugates of indinavir and non-isotopic labels, similar procedures as for the preparation of immunogens are employed.

Alternatively, the activated haptens may be conjugated to amino or thiol groups on enzymes to prepare labels for ELISA application. Some examples of useful enzymes for ELISA for which conjugates are well-known in the art are horseradish peroxidase (HRP), alkaline phosphatase and β-galactosidase. Conjugates of proteins including enzymes are typically prepared in a buffered mixture of water and water miscible organic solvents followed by dialysis analogous to the conditions for preparation of immunogens. In the case of latex agglutination assays, conjugates with aminated dextran carriers having molecular weights between 10 kD and 300 kD, preferably 40 kD, are especially useful. These conjugates are prepared in buffered solvent mixtures as above or in an anhydrous organic solvent such as DMSO containing a tertiary amine such as triethylamine to promote the reaction. In the case of labels of small molecular weight, i.e., less than 1 kD, reaction conditions are adjusted according to the nature of the label. One label which is particularly preferred is biotin in combination with labeled avidin or streptavidin. The versatility of (strept)avidin/biotin systems for non-isotopic detection is well known in the art of bio-conjugate chemistry (see Hermanson, ibid.). A variety of enzyme- and fluorophore-labeled conjugates of avidin and streptavidin are commercially available to detect biotin-labeled substances in a high affinity interaction. Furthermore, a variety of biotinylating agents are commercially available to react with activated functionalities A. For example, a biotin-amine derivative may be reacted with activated haptens of the invention in which A is an active ester, isocyanate or isothiocyanate to give biotin amide, urea and thiourea conjugates respectively. These coupling reactions are typically carried out in a dipolar aprotic solvent such as DMF or DMSO containing an organic base such as triethylamine at room temperature for 0.5 to 5 days. The biotin conjugates are preferentially isolated by chromatographic methods such as reversed phase HPLC.

Other preferred labels are fluorophores such as fluorescein, rhodamine, TEXAS RED, dansyl, and cyanine dyes, e.g., Cy-5, of which many activated derivatives are commercially available. Generally, these conjugates may be prepared similarly as biotin conjugates in a dipolar aprotic solvent containing a tertiary amine followed by chromatographic isolation.

It is also possible to use a reporter group as label which is indirectly coupled to a detection system. One example is biotin as described above. Another example is mycophenolic acid derivatives for inhibition of inosine monophosphate dehydrogenase as described in PCT publication WO 200101135, published Jan. 4, 2001.

It will be obvious to those skilled in the art that there are other possibilities for non-isotopic labels including electrochemiluminescent labels such as ruthenium bipyridyl derivatives, chemiluminescent labels such as acridinium esters, electrochemical mediators, and a variety of microparticles and nanoparticles which can be used for the invention after suitable introduction of suitable nucleophilic groups on the label, e.g., amines or thiols, for reaction with activated groups A on the HIV protease inhibitor activated hapten.

In the examples that follow, numbers in boldface type refer to the corresponding structure shown in the drawings. These examples are presented for illustration only without any intent to limit the invention.

Specific Embodiments

All solvents were from J. T. Baker unless otherwise stated. Analytical reverse phase RP-HPLC analyses were performed on an Agilent HP1100 LC/MS system configured with a diode-array detector and a quaternary pump. The LC/MS analyses were performed with a Vydac 218TP54 column (300A, 5µ; C18, 4.6 mm×250 mm) equipped with a Phenomenex KJO-4282 guard kit with AJO-4287 (C-180DS) cartridge. Chromatographic stream ported postcolumn into the MS detector. The MSD utilized was run in electrospray positive mode "ES (+) mode".

Lyophilization of HPLC fractions, unless otherwise stated, involved evaporation of acetonitrile under reduced pressure followed by freezing of the aqueous residue using, for example, a dry ice/acetone bath, followed by freeze-drying using a lyophilizer.

Preparative HPLC used one of the following Varian DYNAMAX (Rainin) radial compression columns. HPLC work was performed using a gradient system of water-acetonitrile containing 0.1% trifluoroacetic acid.

R00083221C (Microsorb 60-8, C-18; 250 mm×21.4 mm) with a Varian DYNAMAX (Rainin) guard module R00083221G (C-18, 8µ).

R00083241C (Microsorb 60-8, C-18; 250 mm×41.4 mm) with a Varian DYNAMAX (Rainin) guard module R00083241G (C-18, 8µ).

EXAMPLE 1

N-(1(S), 2(R)-2,2-dimethyl indanyloxazole)-2(R)-(phenylmethyl)-4(S)-hydroxy-5-[1-[4-(3-pyridylmethyl)-2(S)-(N-tert-butyl carbamoyl)piperazinyl]] pentanamide (7)

A flask was equipped with a magnetic stir bar, a reflux condenser and a septum to which an argon gas inlet was attached. The reaction flask was charged with 1 g (1.4 mmol) of indinavir sulfate (1), 33 ml (28.7 mmol) of isopropyl acetate, 10 ml of anhydrous DMF, 2.0 ml (52.5 mmol) of 2-methoxypropene followed by 1.8 gm (15.5 mmol) of pyridinium p-toluene sulfonate all at once at room temperature. The reaction was then stirred and heated at 40° C. for 1.5 hours. The reaction progress was monitored by LC/MS, which indicated the completion of reaction. The reaction mixture was then cooled to room temperature, 1.0 gm lithium hydroxide monohydrate was added and the reaction mixture was allowed to stir for about 5 min. The solvent was removed on a rotary evaporator under reduced pressure. The resulting mass was then redissolved in water and extracted with ethyl acetate. The organic phases were combined and dried over anhydrous $MgSO_4$, filtered and the solvent removed on a rotary evaporator. The crude oil was then purified on a silica gel column eluting with 20:1 $CHCl_3$: MeOH. Fractions containing product at Rf0.43 were collected, the solvent was removed on a rotary evaporator and dried under vacuum to give the product as an off white colored powder in 86% (0.72 gm) yield, MS (m/z) 654.4 (M+H). See FIG. 5.

EXAMPLE 2

N-(1(S), 2(R)-2,2-dimethyl indanyloxazole)-2(R)-(phenylmethyl)-4(S)-benzoyl-5-[1-[4-(3-pyridylmethyl)-2(S)-(N-tert-butyl carbamoyl)piperazinyl]] pentanamide (8)

A flask was equipped with a magnetic stir bar and a septum to which an argon gas inlet was attached. The flask was charged with 0.67 g (0.44 mmol) of 7, 10 ml dry DMF, 738 µL (5.3 mmol) of Et3N. The mixture was heated up to 65° C., and at that temperature 1.0 gm (4.4 mmol) of benzoic anhydride dissolved in 5 ml dry DMF was added dropwise. The reaction mixture was then heated to 80° C. for 3 days and the reaction progress was monitored by LC/MS. The reaction mixture was cooled to room temperature and the solvent was removed under reduced pressure. The crude oil was then purified by a preparative HPLC using a gradient run with a solvent system of acetonitrile-water containing 0.1% trifluoroacetic acid. Fractions containing product were collected and lyophilized to give 0.30 gm of the desired product in 89% yield. MS (EI): 758.4 (M+H). See FIG. 5.

EXAMPLE 3

N-(2R-Hydroxy-1(S)-indanyl)-2R-(phenylmethyl)-4(S)-benzoyl-5-[1-[4-(3-pyridylmethyl)-2(S)-(N-tert-butylcarbamoyl)piperazinyl]]pentanamide (9)

A flask was equipped with a magnetic stir bar and a septum to which an argon gas inlet was attached. The flask was charged with the protected indinavir derivative 8 followed by 10 ml of 1:1 mixture of trifluoroacetic acid: dichloromethane. The reaction was stirred at room temperature for 2 hours. LC/MS of the crude material showed that the reaction had gone to completion. The solvent was then removed on a high vacuum rotary evaporator and the crude material was purified on a preparative HPLC by using a gradient run with a solvent system of acetonitrile-water containing 0.1% trifluoroacetic acid. The fractions containing product were collected and lyophilized to give 77% (0.22 gm) of the desired product 9. MS (EI): 741.3 [(M+H)+Na], 718.3 (M+H), 586.3, 359.7, 298.7, 133.1, HRMS: Calculated for C43H51N5O5: 718.3963; Found: 718.3967, [α]20D=−28.42° (C=1.034, $CH_2Cl_2$). See FIG. 5.

EXAMPLE 4

N-(2(R)-(4-formylamino Butyric Acid Ethyl Ester)-1(S)-indanyl)-2(R)-(phenylmethyl)-4(S)-benzoyl-5-[1-[4-(3-pyridylmethyl)-2(S)-(N-tert-butylcarbamoyl)piperazinyl]]Pentanamide (10)

A flask was equipped with a magnetic stir bar and a septum to which an argon gas inlet was attached. The flask was charged with 220 mg (0.30 mmol) of indinavir derivative 9 and 1.2 ml (9.2 mmol) of Et3N in dry THF. To the reaction mixture 0.90 ml (11.5 mmol) of ethyl-4-isocyanato butyrate was added and the reaction was then heated at 80° C. for 2 days. LC/MS showed product formation. The reaction was cooled to room temperature, solvent removed on a rotary evaporator and the residue was purified on preparative HPLC by using a gradient run with a solvent system of acetonitrile-water containing 0.1% trifluoroacetic acid. Fractions containing product were combined and lyophilized to give 87% (235 mg) of product. MS (EI): 875.4 (M+H), 438.3, 359.7, 158.1. See FIG. 5.

EXAMPLE 5

N-(2(R)-(4-formylamino butyric acid)-1(S)-indanyl)-2(R)-(phenylmethyl)4(S)-hydroxy-5-[1-[4-(3-pyridylmethyl)-2(S)-(N-tert-butylcarbamoyl)piperazinyl]]pentanamide (11)

To a flask containing 235 mg (0.268 mmol) of 10 was added 10 mL of methanol and 10 ml of aqueous 1N NaOH. The reaction was stirred at room temperature for 1 day. The reaction progress was monitored by LC/MS which indicated complete product formation. The reaction was concentrated under reduced pressure, and the residue was purified by preparative HPLC by using a gradient run with a solvent system of acetonitrile-water containing 0.1% trifluoroacetic acid. Fractions containing product were combined and lyophilized to give 96% (190 mg) of product 11. MS (EI): 766.3 (M+Na), 743.3 (M+H), 372.1, 307.7, 60.1. See FIG. 5.

EXAMPLE 6

N-(2(R)-[(4-formylamino butyric acid-N-succinimidyl ester)]-1(S)-indanyl)-2(R)-(phenylmethyl)-4(S)-hydroxy-5-[1-[4-(3-pyridylmethyl)-2(S)-(N-tert-butylcarbamoyl)piperazinyl]]pentanamide (12)

A 50-ml round bottom flask was equipped with a magnetic stir bar and a septum with an argon gas inlet. The flask was charged with 190 mg (0.25 mmol) of 11, 5 ml anhydrous THF, 0.133 ml (0.74 mmol) of dry diisopropyl ethyl amine and 207 mg (0.69 mmol) of [O-(N-succinimidyl-N,N,N',N'-tetramethyluronium ]tetrafluoroborate at 0° C. The reaction mixture was allowed to warm up to room temperature, stirred at that temperature for 24 hours and concentrated under reduced pressure. The residue was purified on a preparative HPLC by using a gradient system of water-acetonitrile containing 0.1% trifluoroacetic acid. Fraction containing were combined, and lyophilized to give 57 mg (27%) product 12 as a white solid. MS (m/z): 840.4 (M+H), 725.4, 482.3, 420.7, 298.7, 130.2. See FIG. 5.

EXAMPLE 7

Indinavir-BSA Conjugate Out of Indane Ring (13A)

Figure 6:
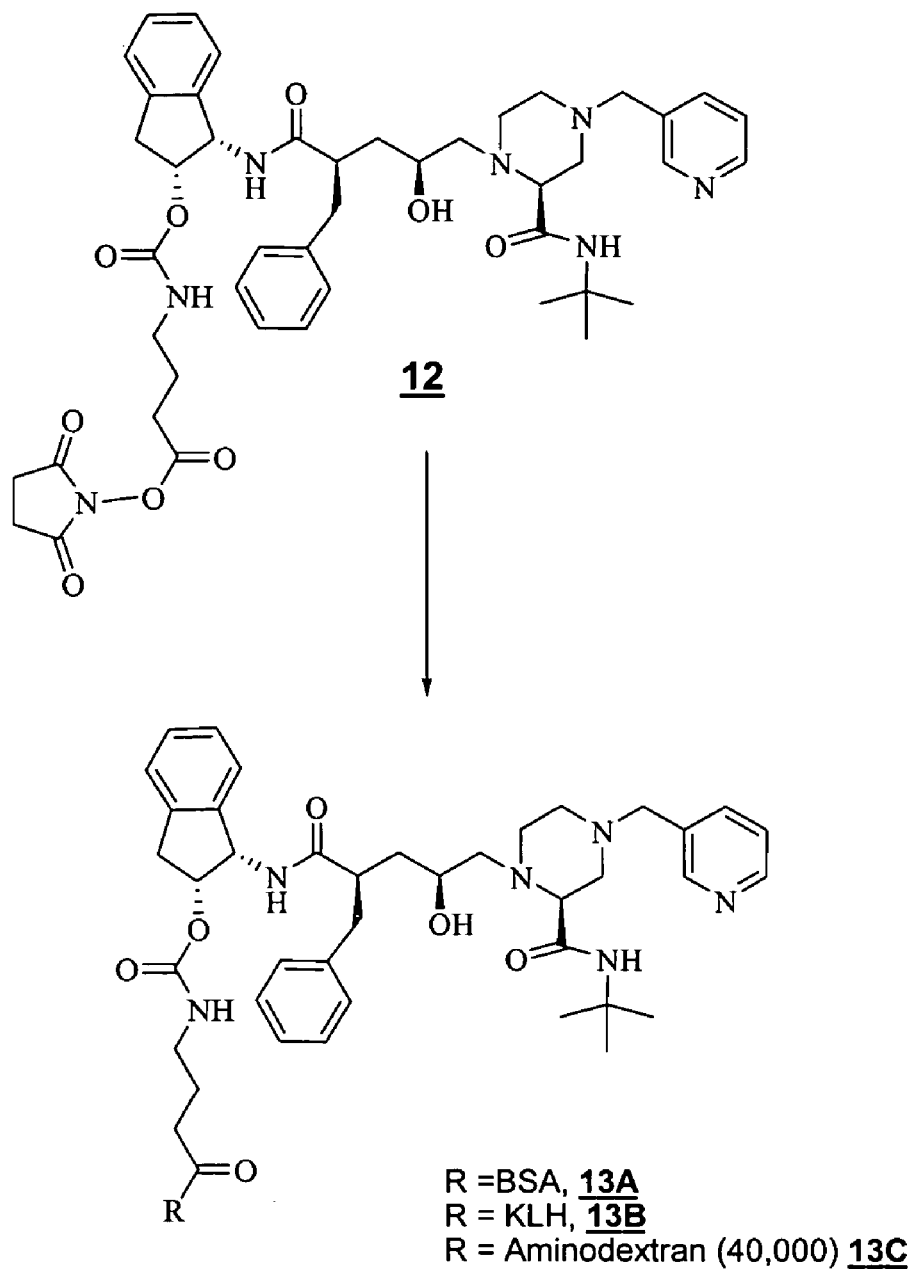
FIG. 6 illustrates a scheme for synthesis of BSA, KLH, and aminodextran derivatives of the activated hapten 12 as described in Examples 7, 8, and 26, respectively.

A solution of 0.34 g of bovine serum albumin (BSA) in 5.8 mL of 50 mM potassium phosphate (pH 7.5) was cooled in an ice-bath. To the solution was added 8.5 mL of DMSO dropwise and the reaction mixture was maintained below room temperature. To the protein solution was added a solution of 15 mg (0.017 mmol) of indinavir derivative (12) in 1.5 mL of anhydrous DMF dropwise. The reaction mixture was allowed to stir at room temperature 24 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50 % DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature followed by 6 changes with 50 mM potassium phosphate (pH 7.5) at 4° C. (1 L each for at least 6 hours each). The protein concentration was determined to be 14 mg/mL using Biorad Coomassie blue protein assay (Bradford, M., Anal. Biochem. 72, 248, 1976). A total of 21.5 mL of the conjugate was obtained. See FIG. 6.

EXAMPLE 8

Indinavir-KLH Conjugate Out of Indane Ring (13B)

A solution of 72 mg of keyhole limpet hemocyanin (KLH) in 2 ml of 50 mM potassium phosphate (pH 7.5) was cooled in an ice-bath. To the reaction mixture 4.7 mL of DMSO was added to the solution dropwise and the reaction temperature was maintained below room temperature. Then a solution of 16.7 mg (0.018 mmol) of 5 in 670 µL of DMF was added to the protein solution dropwise. The mixture was allowed to stir at room temperature 18 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature. The protein concentration was determined to be 11 mg/mL using BioRad Coomassie blue protein assay. The extent of available lysine modification was determined to be 46% by the TNBS method (Habeeb AFSA, Anal. Biochem. 14, 328–34, 1988). See FIG. 6.

EXAMPLE 9

N-(2(R)-hydroxy-1(S)-indanyl)-2(R)-(phenylmethyl)-4(S)-hydroxy-5-[1-[4-(3-{1-(3-tert-butoxycarbonyl-propyl)}pyridylmethyl)-2(S)-(N-tert-butylcarbamoyl)piperazinyl]]pentanamide trifluoroacetate (3)

To a flask equipped with a magnetic stir bar, a septum to which an argon gas inlet was attached was added 0.2 gm (0.28 mmol) indinavir sulfate, 5-ml dry DMF followed by 72 µl (0.56 mmol) of Et3N. To this stirring solution was added 0.43 gm (1.96 mmol) of t-butyl-4-bromobutyrate via a syringe. The contents of the flask were then heated at 80° C. for 16 hours. LC/MS of the crude material indicated the product formation, the reaction mixture was cooled to room temperature and the solvent removed on a rotary evaporator. The residue was then purified on a preparative HPLC by using a gradient system of water-acetonitrile containing 0.1% trifluoroacetic acid. Fractions containing product were combined and lyophilized to give 71% (0.174 gm) of the monoalkylated product. At this point the structure of the product was unclear, as there were multiple sites where the alkylation would have occurred.

Serendipitously, the alkylation of the electrophile occurred at the nitrogen of the pyridine ring to give the corresponding pyridinium cation. The structure of which was elucidated using 1H NMR and NOE experiments. The methylene protons next to the pyridinium nitrogen show as a triplet at 4.70 ppm. These methylene protons (at 4.70 ppm) when irradiated showed an NOE effect on the two Hα methine protons adjacent to the pyridyl nitrogen atom at 8.9 ppm and 9.02 ppm which is distinctively indicative of an alkylated pyridine ring and thus confirming the structure of the product 3. MS (EI): 756.4 (M+H), 378.7, 330.2, 133.1, HRMS: Calculated for C44H62N5O6: 756.4695, Found: 756.4693. See FIG. 7.

EXAMPLE 10

N-(2(R)-hydroxy-1(S)-indanyl)-2(R)-(phenylmethyl)-4(S)-hydroxy-5-[1-[4-(3-{1-( 3-butyric acid)}pyridylmethyl)-2(S)-(N-tert-butylcarbamoyl)piperazinyl]]pentanamide trifluoroacetate (4)

To 0.165 gm (0.19 mmol) of 3, was added 10 ml of 1:1 trifluoroacetic acid: dichloromethane. The reaction was stirred for 30 min at room temperature. LC/MS of the crude reaction mixture showed only the product peak. The reaction mixture was concentrated on a rotary evaporator. The residue was then purified on a preparative HPLC by using a gradient system of water-acetonitrile containing 0.1% trifluoroacetic acid. Fractions containing product were combined and lyophilized to give 38% (0.059 gm) product 4, MS (EI): 700.3 (M+H), 568.3, 551.3, 350.8, 341.7, 133.1, HRMS: Calculated for C40H54N5O6: 700.4069, Found: 700.4075, $[\alpha]20D=+30.5\ °(C=1.0, CH_2Cl_2)$. See FIG. 7.

EXAMPLE 11

N-(2(R)-hydroxy-1(S)-indanyl)-2(R)-(phenylmethyl) 4(S)-hydroxy-5-[1-[4-(3-{1-(4-N-succinimidylbutyrate)}pyridylmethyl-2(S)-(N-tert-butylcarbamoyl) piperazinyl]]pentanamide trifluoroacetate (5)

A 50-ml round bottom flask (previously heat gun dried under vacuum) was equipped with a magnetic stir bar, a septum to which and argon gas inlet was attached. The flask was charged with 20 mg (0.024 mmol) of 4, 5 ml dry THF, 12 μl of Et3N followed by 19.9 mg (0.066 mmol) of [O-(N-succinimidyl)-N,N,N',N'-tetramethyl uronium]tetrafluoroborate all at once. The reaction was stirred at 0° C. and was warmed up to room temperature over a period of 6 hours. LC/MS of the crude reaction mixture indicated the product formation and the reaction mixture was concentrated on a rotary evaporator. The residue was purified on a preparative HPLC using a gradient system of water-acetonitrile containing 0.1% trifluoroacetic acid. Fractions containing product were combined and lyophilized to give 94.14% (21.0 mg) product. MS (EI): 797.3 (M+H), 648.3, 399.2, 324.7, HRMS: Calculated for C44H57N6O8: 797.4233, Found: 797.4237, $[\alpha]_D^{20}=+44.06°(C=1.0, CH_2Cl_2)$. See FIG. 7.

EXAMPLE 12

Indinavir-BSA Conjugate Out of Pyridyl Ring (6A)

A solution of 0.23 g of bovine serum albumin (BSA) in 2.4 mL of 50 mM potassium phosphate (pH 7.5) was cooled in an ice-bath. To the solution was added 4.25 mL of DMSO dropwise and the reaction mixture was maintained below room temperature. To the protein solution was added a solution of 15 mg (0.016 mmol) of indinavir derivative (5) in 1.5 mL of anhydrous DMF dropwise. The reaction mixture was allowed to stir at room temperature 24 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50 % DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature followed by 6 changes with 50 mM potassium phosphate (pH 7.5) at 4° C. (1 L each for at least 6 hours each). The protein concentration was determined to be 12 mg/mL using Biorad Coomassie blue protein assay. A total of 18 mL of the conjugate was obtained. See FIG. 7.

EXAMPLE 13

Indinavir-KLH Conjugate Out of Pyridyl Ring (6B)

A solution of 54 mg of keyhole limpet hemocyanin (KLH) in 1.5 ml of 50 mM potassium phosphate (pH 7.5) was cooled in an ice-bath. To the reaction mixture 4.7 mL of DMSO was added to the solution dropwise and the reaction temperature was maintained below room temperature. Then a solution of 16.7 mg (0.018 mmol) of 5 in 670 μL of DMF was added to the protein solution dropwise. The mixture was allowed to stir at room temperature 18 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature. The protein concentration was determined to be 11 mg/mL using BioRad Coomassie blue protein assay. The extent of available lysine modification was determined to be 46% by the TNBS method. See FIG. 7.

EXAMPLE 14

M6-indinavir Metabolite (2)

Figure 8:
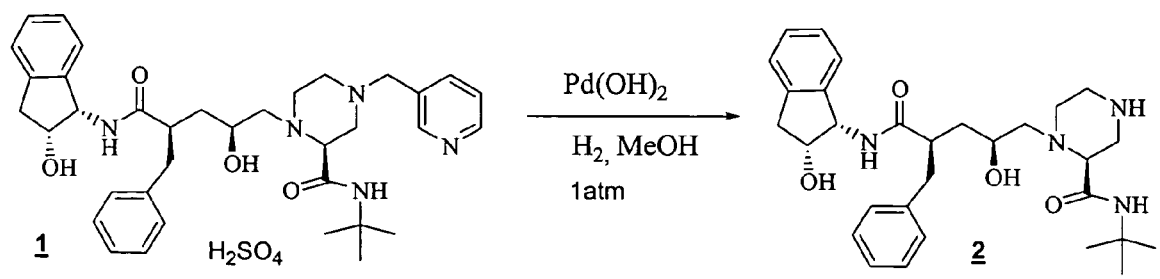
FIG. 8 illustrates a scheme for synthesis of indinavir metabolite M6 (2) in one step from indinavir in the presence of hydrogen gas and palladium catalyst as described in Example 14.

To a flask equipped with a magnetic stir bar was added 0.30 gm (0.4214 mmol) indinavir sulfate (1), 30 ml methanol followed by 40 mg of 20 wt % Pd(OH)$_2$/C catalyst. The air in the reaction vessel was removed under vacuum and hydrogen gas was introduced at 1 atm. The reaction was then stirred at room temperature for 16 hours. At that time LC/MS of the crude material indicated completion of the reaction. It was then filtered through a pad of CELITE, the solvent was removed on a rotary evaporator and dried under vacuum to give 99% (0.2187 gm) product. MP=147° C., TLC (silica gel) Rf=0.35 (MeOH), MS (EI): 523.3 (M+H), HRMS: Calculated for C30H42N4 O4: 523.3279, Found: 523.3282, $[\alpha]_D^{20}=+13.32°$ (C=1.036, CH$_2$Cl$_2$). See FIG. 8.

EXAMPLE 15

N-(2(R)-hydroxy-1(S)-indanyl)-2(R)-(phenylmethyl)-4(S)-hydroxy-5-[1-[4-(4-benzoic acid methy)-2(S)-(N-tert-butylcarbamoyl)piperazinyl]]pentanamide (14)

Figure 9:
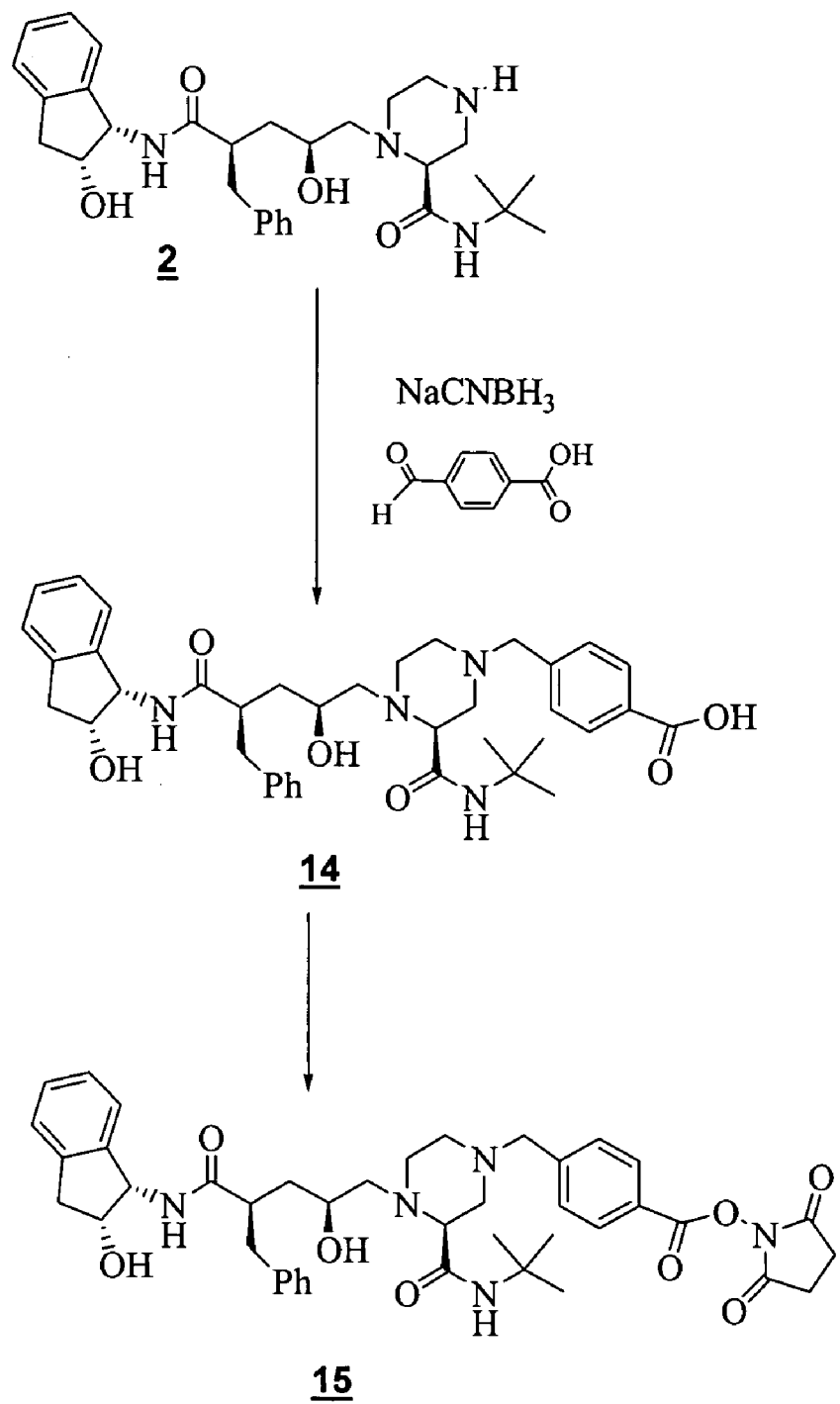
FIG. 9 illustrates a scheme for synthesis of indinavir derivatives having a substituted aromatic linking group out of the piperazine nitrogen of M6 as described in Examples 15 and 16.

To a round bottom flask equipped with a magnetic stir bar was added 70 mg (0.1346 mmol) of indinavir M6 (@ in dry CH$_2$Cl$_2$, followed by 24 mg (0.16 mmol) of 4-carboxy benzaldehyde and 16.8 mg (0.26 mmol) of sodium cyanoborohydride. The reaction mixture was stirred at room temperature for one day. It was then quenched with water and extracted with 3×20 ml CH$_2$Cl$_2$. The organic phases were combined and dried over anhydrous MgSO$_4$, filtered and the solvent removed on a rotary evaporator. The crude mixture was then purified on a silica gel column eluting with 1:1 hexane:ethyl acetate to give 80% (71 mg). MS (m/z)= 657.3 (M+H). See FIG. 9.

EXAMPLE 16

4-{3-tert-Butylcarbamoyl-4-[2-hydroxy-4-(2-hydroxy-indan-1-ylcarbamoyl)-5-phenyl-pentyl]-piperazin-1-ylmethyl}-benzoic acid 2,5-dioxo-pyrrolidin-1-yl ester (15)

A 50-ml round bottom flask (previously heat gun dried under vacuum) is equipped with a magnetic stir bar, a septum to which and argon gas inlet is attached. The flask is charged with 20 mg (0.03 mmol) of 14, 5 ml dry THF, 12 µl Et3N followed by 19.9 mg (0.06 mmol) of [O-(N-succinimidyl)-N,N,N',N'-tetramethyl uronium]tetrafluoroborate all at once. The reaction is stirred at 0° C. and is warmed up to room temperature and allowed to stir at that temperature 6 hours. The reaction mixture is concentrated on a rotary evaporator and is purified on a preparative HPLC to give desired product. See FIG. 9.

EXAMPLE 17

N-(2(R)-hydroxy-1(S)-indanyl)-2(R)-(phenylmethyl)-4(S)-hydroxy-5-[1-[4-butyric acid]]-2(S)-]N-butylcarbamoyl)piperaznyl]] pentanamide (16)

To a flask equipped with a magnetic stir bar and a septum was added 0.1 g (0.19 mmol) of indinavir M6 (2) 10 ml dry $CH_2Cl_2$, followed by 0.012 g (0.19 mmol) of sodium cyano borohydride and 0.025 g (0.23 mmol) of succinic semialdehyde (15% by weight in water). The reaction was stirred at room temperature overnight. The reaction was then quenched with 20 ml deionized water, acidified with 3 N HCl, and extracted with 3×20 ml of diethyl ether. The organic phases were combined and dried over anhydrous $MgSO_4$, filtered and the solvent removed on a rotary evaporator. It was then purified on a preparative HPLC using a gradient system of water-acetonitrile containing 0.1% trifluoroacetic acid. Fractions containing product were combined and lyophilized to give 68 mg (42%) yield. MS (m/z)=609.3 (M+H), 477.3, 133.1. See FIG. 10.

EXAMPLE 18

4-{3-tert-Butylcarbamoyl-4-[2-hydroxy-4-(2-hydroxy-indan-1-ylcarbamoyl)-5-phenyl-pentyl]-piperazin-1-yl}-butyric acid 2,5-dioxo-pyrrolidin-1-yl ester (17)

A 50 ml dry round bottom flask is equipped with a magnetic stir bar, a septum to which and argon gas inlet is attached. The flask is charged with 0.032 mmol (20 mg) of 16, 5 ml dry THF, 12 µl Et3N followed by 0.06 mmol (19.9 mg) [O-(N-succinimidyl)-N,N,N',N'-tetramethyl uronium] tetrafluoroborate all at once. The reaction is stirred at 0° C. and is gradually warmed up to room temperature over a period of 6 hours. The reaction mixture is concentrated on a rotary evaporator and is purified on a preparative HPLC to give the desired active ester 17. See FIG. 10.

EXAMPLE 19

N-(2(R)-hydroxy-1(S)-indanyl)-2(R)-(phenylmethyl)-4(S)-hydroxy-5-[1-[4(2-methyl picolate methy)]]-2(S)-(N-tert-butylcarbamoyl)piperaziny]] pentanamide (18)

Figure 11:
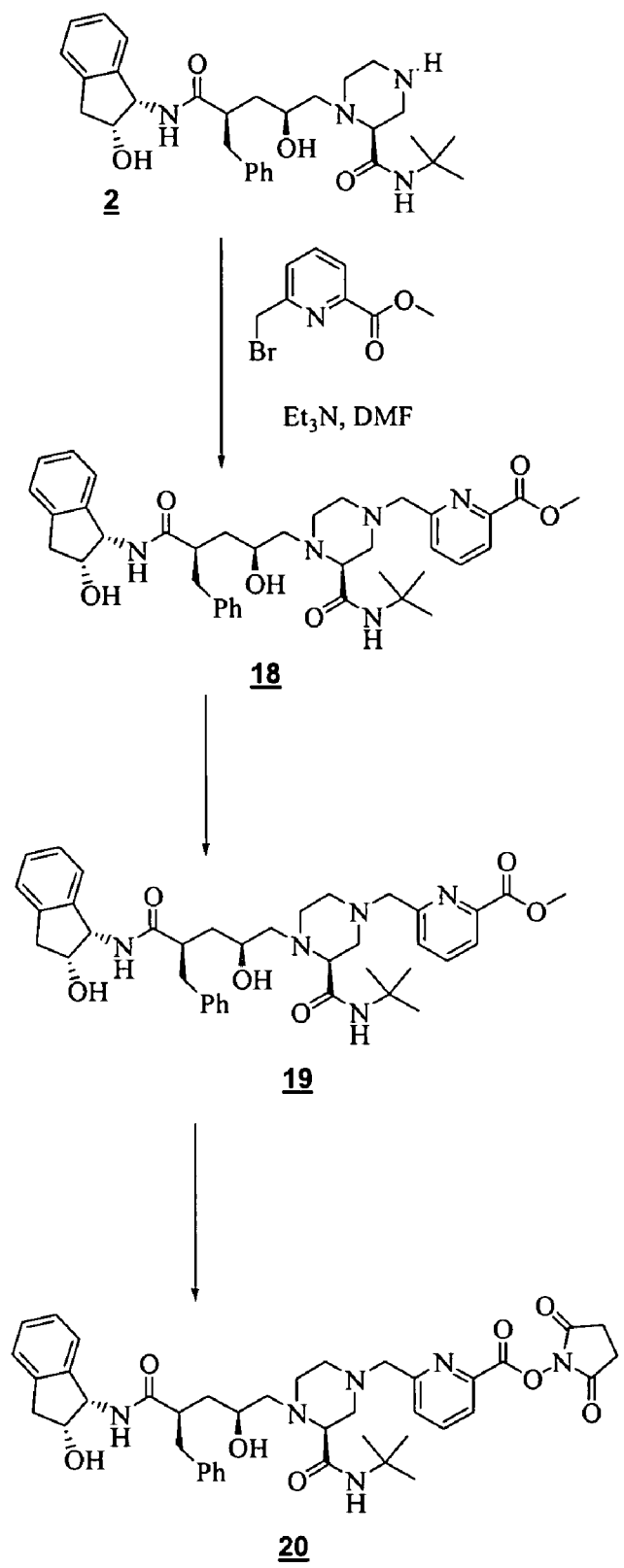
FIG. 11 illustrates a scheme for synthesis of indinavir derivatives having a pyridyl linking group out of the piperazine nitrogen of M6 as described in Examples 19–21.

To a flask equipped with a magnetic stir bar and a septum was added 50 mg (0.095 mmol) of indinavir M6 (2), 4-ml dry DMF, 15 µl dry Et3N, followed by 0.024 g (0.10 mmol) of 2-bromomethylpyridine-6-carboxlylic acid methyl ester. The reaction was stirred at room temperature for 3 hours and the reaction progress was monitored by LC/MS. The solvent was then removed on high vacuum and the material was purified on preparative HPLC. Fractions containing product were combined and lyophilized to give 24.7 mg (38%) product. MS (m/z)=694.3 (M+Na), 672.3 (M+H), 540.3, 336.7, 133.1. See FIG. 11.

EXAMPLE 20

6-{3-tert-Butylcarbamoyl-4-[2-hydroxy-4-(2-hydroxy-indan-1-ylcarbamoyl)-5-phenyl-pentyl-piperazin-1-ylmethyl}-pyridine-2-carboxylic acid (19)

To a flask containing 25 mg (0.037 mmol) of 18 is added 3 mL of methanol and 3 ml of aqueous 1 N NaOH. The reaction is stirred at room temperature for 1 day. LC-MS shows complete product formation. The reaction mixture is concentrated under reduced pressure, and the residue is purified by preparative HPLC using a gradient run with a solvent system of acetonitrile-water containing 0.1% trifluoroacetic acid. Fractions containing product are combined and lyophilized to give desired product 19. See FIG. 11.

EXAMPLE 21

6-{3-tert-Butylcarbamoyl-4-[2-hydroxy-4-(2-hydroxy-indan-1-ylcarbamoyl)-5-phenyl-pentyl]-piperazin-1-ylmethyl}-pyridine-2-carboxylic acid 2,5-dioxo-pyrrolidin-1-yl ester (20)

A 50-ml dry round bottom flask is equipped with a magnetic stir bar, a septum to which and argon gas inlet is attached. The flask is charged with 20 mg (0.030 mmol) of the indinavir acid 19, 5 ml dry THF, 12 µl Et3N followed by 19.9 mg (0.06 mmol) of [O-(N-succinimidyl)-N,N,N',N'-tetramethyl uronium]tetrafluoroborate all at once. The reaction is stirred at 0° C. and is gradually warmed up to room temperature. The reaction mixture is stirred at room temperature for 6 hours and concentrated on a rotary evaporator. The residue is purified on a preparative HPLC using a gradient run with a solvent system of acetonitrile-water containing 0.1% trifluoroacetic acid. Fractions containing product are combined and lyophilized to give desired product 20. See FIG. 11.

EXAMPLE 22

5-{3-tert-Butylcarbamoyl-4-[2-hydroxy-4-(2-hydroxy-indan-2-ylcarbamoyl)-5-phenyl-pentyl]-piperazin-1-methyl}-pyridine-2-carboxylic acid ethyl ester (21)

To a round bottom flask equipped with a magnetic stir bar and a septum is added 70 mg (0.13 mmol) of indinavir M6 (2) in dry $CH_2Cl_2$, followed by 0.16 mmol (26 mg) of 5-formyl-2-pyridine carboxylic acid ethyl ester (U.S. Pat. No. 4,526,787) and 16.8 mg (0.26 mmol) of sodium cyanoborohydride. The reaction mixture is stirred at room temperature for one day. The reaction mixture is quenched with water and extracted with 3×20 ml $CH_2Cl_2$. The organic phases are combined and dried over anhydrous $MgSO_4$, filtered and the solvent removed on a rotary evaporator. The crude mixture is then purified on a silica gel column to give desired product. See FIG. 12.

EXAMPLE 23

5-{3-tert-Butylcarbamoyl-4-[2-hydroxy-4-(2-hydroxy-indan-1-ylcarbamoyl)-5-phenyl-pentyl]-piperazin-1-ylmethyl}-pyridine-2-carboxylic acid (22)

To a flask containing 25 mg (0.037 mmol) of 21 is added 3 mL of methanol and 3 ml of aqueous 1 N NaOH. The reaction is stirred at room temperature for 1 day. LC-MS shows complete product formation. The reaction is concentrated under reduced pressure, and the residue is purified by preparative HPLC by using a gradient run with a solvent system of acetonitrile-water containing 0.1% trifluoroacetic acid. Fractions containing product are collected, the solvent is removed on a rotary evaporator and lyophilized to give desired product. See FIG. 12.

EXAMPLE 24

5-{3-tert-Butylcarbamoyl-4-[2-hydroxy-4-(2-hydroxy-indan-1-ylcarbamoyl)-5-phenyl-pentyl]-piperazin-1-ylmethyl}-pyridine-2-carboxylic acid 2,5-dioxo-pyrrolidin-1-yl (23)

To a solution of 20 mg (0.030 mmol) of 22 in 5 ml dry THF is added 12 μl Et3N followed by 19.9 (0.06 mmol) of [O-(N-succinimidyl)-N,N,N',N'-tetramethyl uronium]tetrafluoroborate. The reaction is stirred at 0° C. and is warmed up to room temperature. The reaction mixture is stirred at room temperature for 6 hours and concentrated on a rotary evaporator. The residue is purified on a preparative HPLC using a gradient run with a solvent system of acetonitrile-water containing 0.1% trifluoroacetic acid. Fractions containing product are combined and lyophilized to give desired product. See FIG. 12.

EXAMPLE 25

Principle of Immunoassay Format

The assay format described here for indinavir is a homogeneous microparticle immunoassay. It is a two-reagent system for the detection of indinavir in serum. Kinetic interaction of microparticles in a solution (KIMS) has been measured using Roche Diagnostics/Hitachi families of automated analyzers. In this technology indinavir antibody has been covalently coupled onto the microparticle, and the drug derivative is linked to a macromolecule (aminodextran). A competitive reaction takes place between the drug conjugate and any indinavir in the serum sample for binding to a limited amount of specific indinavir antibody on the microparticle. The kinetic interaction of microparticles in solution is induced by binding of drug conjugate to the antibody on the microparticle and is inhibited by the presence of indinavir in the sample.

Indinayir antibodies were prepared from indinavir immunogens described in U.S. 2004/40127689.

EXAMPLE 26

Indinavir-Aminodextran Conjugate Out of Indane Ring (13C)

Aminodextran (MW 40,000) was prepared according to a procedure described in U.S. Pat. No. 6,653,456. By using TNBS assays, the product was found to contain 5.7 amino groups for every mole of aminodextran.

This aminodextran was used to prepare indinavir-aminodextran conjugate (out of indane ring). To 20 mg of aminodextran was added 1 mL of DMSO at room temperature. The mixture was allowed to stir at room temperature for until all aminodextran went into solution. To the reaction mixture 13 μL (0.092 mmol) of triethylamine was added. The indinavir derivative 12, 8.87 mg (0.010 mmol) was dissolved in 0.44 mL of anhydrous DMSO and added dropwise to the stirred aminodextran solution. The mixture was allowed to stir at room temperature for 48 hours and was transferred into SPECTRA/POR dialysis tubing (MW cut-off 3500) and dialyzed (each dialysis using 1 L volume) according to the following schedule (1 L volume, at least 8 hours each) at room temperature: 80% DMSO, 60% DMSO, 40% DMSO and 20% DMSO in deionized water followed by deionized water.

The solution was taken out of the dialysis tubing and lyophilized to give 15 mg of indinavir-dextran conjugate as a white powder. See FIG. 6.

EXAMPLE 27

Indinavir-Aminodextran Conjugate Out of Pyridine Ring (6C)

This aminodextran was used to prepare indinavir-aminodextran conjugate (out of pyridine ring). To 20 mg of aminodextran was added 1 mL of DMSO at room temperature. The mixture was allowed to stir at room temperature until all aminodextran went into solution. To the reaction mixture 13 μL (0.092 mmol) of triethylamine was added. The indinavir derivative 5, 9.86 mg (0.011 mmol), was dissolved in 0.44 mL of anhydrous DMSO and added dropwise to the stirred aminodextran solution. The mixture was allowed to stir at room temperature for 48 hours and was transferred into SPECTRA/POR dialysis tubing (MW cut-off 3500) and dialyzed (each dialysis using 1 L volume) according to the following schedule (1 L volume, at least 8 hours each) at room temperature: 80% DMSO, 60% DMSO, 40% DMSO, and 20% DMSO in deionized water followed by deionized water. The solution was taken out of the dialysis tubing and lyophilized to give 15 mg of indinavir-dextran conjugate as a white powder. See FIG. 7.

EXAMPLE 28

Preparation of Indinavir Latex Reagent

A 10% (w/v) solid carboxylate-modified latex microparticle (Seradyn) was diluted to 1% (w/v) solid with deionized water. The suspension was centrifuged at 32,600×g for 1 hour at 4° C. The pellet was saved and resuspended by sonication. The 1% latex suspension was washed by centrifugation as described above with 5 volume equivalents of deionized water followed by 5 volume equivalents of wash buffer (50 mM 2-(N-morpholino)-ethanesulfonic acid (MES), pH 5.5). The latex microparticles were stored at 4° C. The latex concentration was determined on Roche Cobas Mira and adjusted to 1% (w/v) with 50 mM MES buffer, pH 5.5.

The washed 1% (w/v) latex was activated with 10 equivalents of N-ethyl-N'-(3-dimethylaminopropyl) carbodiimide (EDC) and 10 equivalents of Sulpho NHS in 50 mM MES, pH 5.5 and 50 mg/mL EDC solution in deionized water. The reaction mixture was stirred for 2 hours at room temperature.

The reaction mixture was centrifuged at 3200×g for 1 hour at 4° C. and the latex pellet was resuspended in 50 mM MOPS, pH 6.4. The latex concentration was measured on Roche Cobas Mira and the latex suspension was adjusted to 1% (w/v).

The desired amount of indinavir monoclonal antibody (0.2 mg of Mab/1% latex, M-2.35.2 and M1.158.8 respectively, (ref: U.S. 200440127689) at each antibody loading was added to 1% (w/v) latex and the latex mixture was stirred at room temperature for 2 h.

The latex mixture was post-blocked by adding 50 mg/mL of BSA in 50 mM MOPS, pH 6.4 and stirring at room temperature overnight.

The latex mixture was centrifuged at 32,600×g for 1 hour at 4° C. and the latex pellet was resuspended in latex storage buffer (50 mM MOPS, 0.1% BSA, 0.09% NaN3, pH 7.2). This is reagent R2.

The latex was washed three times by centrifugation as described above with latex storage buffer. The monodispersity of latex suspension was measured on Roche Cobas Mira. The latex suspension concentration was adjusted to 1.5% and stored at 4° C.

EXAMPLE 29

Indinavir Calibration Curve

Indinavir sulfate was dissolved in 50% ethanol to make a 1 mg/mL stock solution. Two sets of serum calibrators and controls were prepared. Low-set serum calibrators were prepared at concentrations of 0.25, 0.325, 0.75, 1.5 and 3 μg/nL of indinavir from the indinavir stock solution in Roche TDM serum. High-set serum calibrators were spiked with indinavir at concentrations of 0, 0.75, 1.5, 3, and 12 μg/mL.

A conjugate reagent was prepared by making a 0.2 mg/mL of indinavir aminodextran conjugate (13C or 6C) in 180 mM PIPES buffer having pH 7.2 and containing 0.1% polyacrylic acid and 0.1% TWEEN 20 (reagent R1). Preparation of latex reagent R2 has been described above.

An assay was performed using a Hitachi 917 automated analyzer (Roche Diagnostics Corporation, Indianapolis) using 120 μL of the first working reagent (R1) and 160 μL of second working reagent (R2) and 15 μL of sample volume and measuring the absorbance change at wave length of 600 nm.

What is claimed is:

1. A compound having the formula:

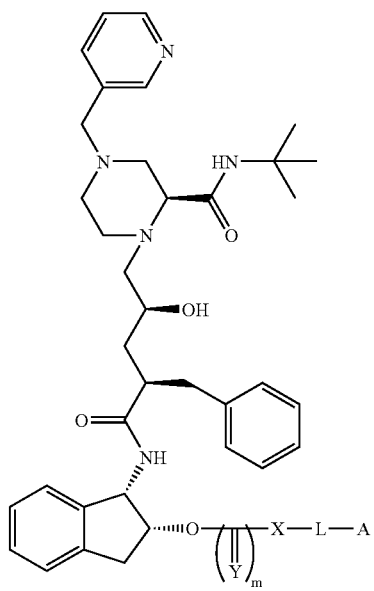

I where Y=O or S, m=1, X=CH$_2$ or NH, L is a linking group comprising 1 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

2. The compound of claim 1 wherein A is an active ester.

3. The compound of claim 1 wherein Y=O, L comprises 3 carbon atoms, X is NH, and A is an active ester.

4. The compound:

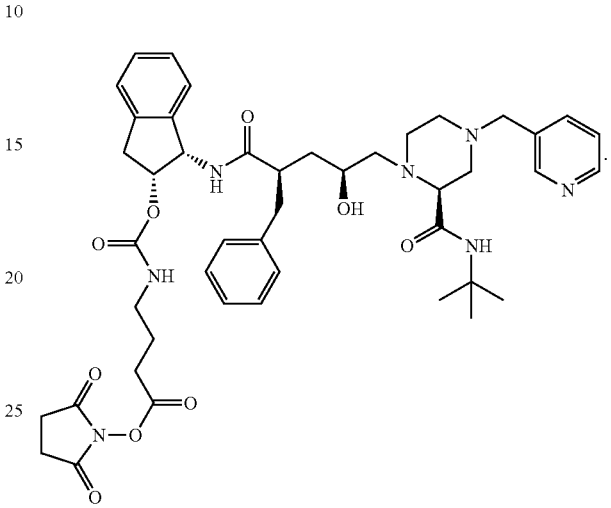

5. A compound having the formula:

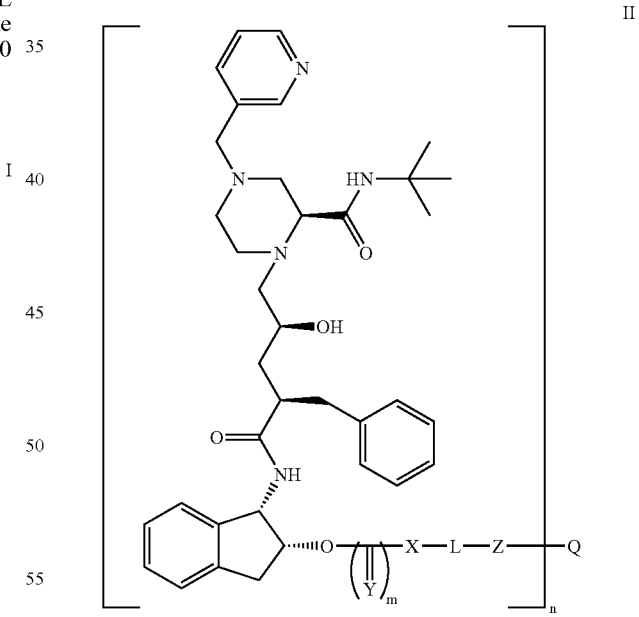

II where Y=O or S, m=1, X=CH$_2$ or NH, L is a linking group comprising 1 to 40 carbon atoms arranged in a straight or a branched chain, saturated or unsaturated, and further comprising up to two ring structures and 0–20 heteroatoms, with the proviso that not more than two heteroatoms may be linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

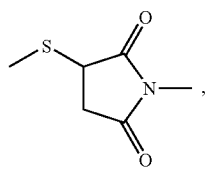

Q is selected from the group consisting of polypeptides, polysaccharides, synthetic polymers, and non-isotopic labels, and n is a number from 1 to 50 per 50 kilodaltons molecular weight of Q.

6. The compound of claim 5 wherein Q is a polypeptide or polysaccharide selected from the group consisting of bovine serum albumin, keyhole limpet hemocyanin, limulus polyphemus hemocyanin, bovine, thyroglobulin, and aminodextran.

7. The compound of claim 5 wherein Y=O, X is NH, L comprises 4 C atoms, and Q is selected from the group consisting of bovine serum albumin, keyhole limpet hemocyanin, and aminodextran.

8. The compound:

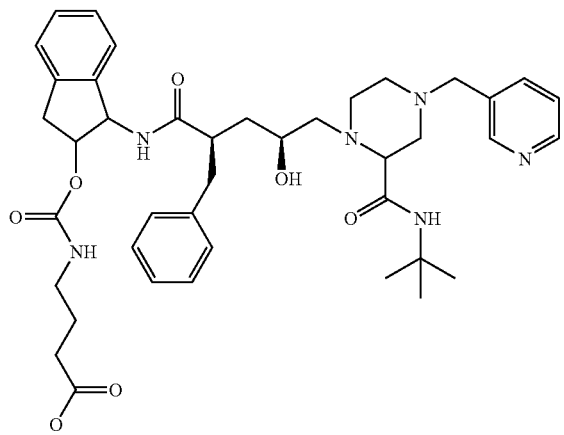

wherein Q is selected from the group consisting of bovine serum albumin, keyhole limpet hemocyanin, and aminodextran.

9. A compound having the formula:

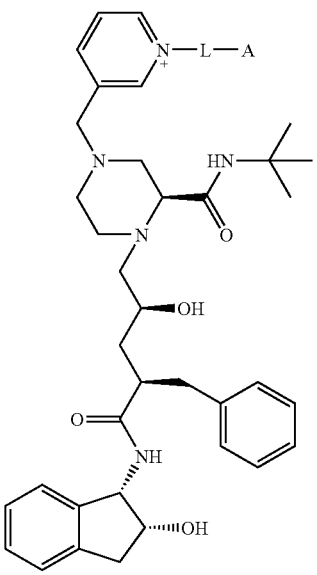

III where L is a linking group comprising 1 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

10. The compound of claim 9 wherein A is an active ester.

11. The compound of claim 10 wherein L comprises 3 carbon atoms.

12. The compound:

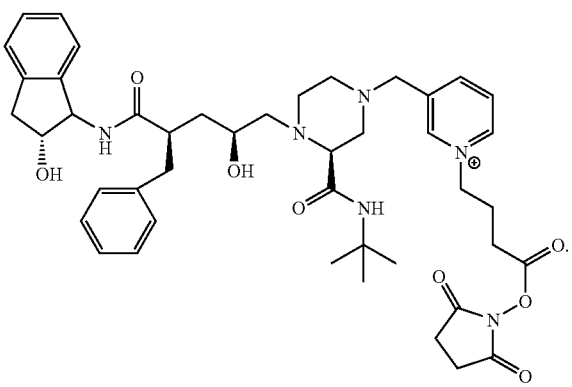

13. A compound having the formula:

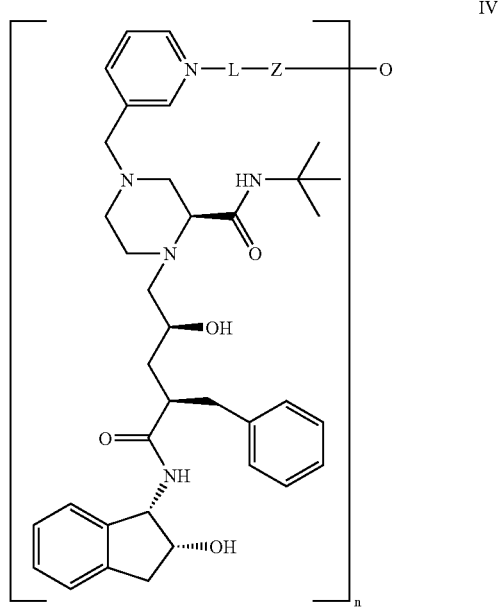

IV where L is a linking group comprising 1 to 40 carbon atoms arranged in a straight or a branched chain, saturated or unsaturated, and further comprising up to two ring structures and 0–20 heteroatoms, with the proviso that not more than two heteroatoms may be linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

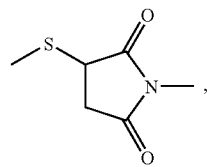

Q is selected from the group consisting of polypeptides, polysaccharides, synthetic polymers, and non-isotopic labels, and n is a number from 1 to 50 per 50 kilodaltons molecular weight of Q.

14. The compound of claim 13 wherein Q is a polypeptide or polysaccharide selected from the group consisting of bovine serum albumin, keyhole limpet hemocyanin, limulus polyphemus hemocyanin, bovine, thyroglobulin, and aminodextran.

15. The compound of claim 13 wherein L comprises 4 C atoms.

16. The compound:

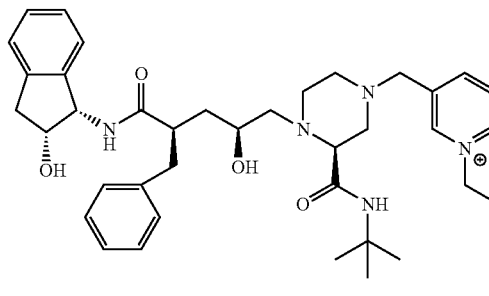

wherein Q is selected from the group consisting of bovine serum albumin, keyhole limpet hemocyanin, and aminodextran.

17. A compound having the formula:

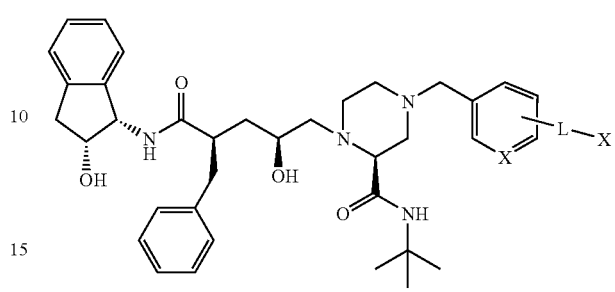

where X is N or C, L is a linking group comprising 1 to 40 carbon atoms arranged in a straight or a branched chain, saturated or unsaturated, and containing up to two ring structures and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

18. A compound having the formula:

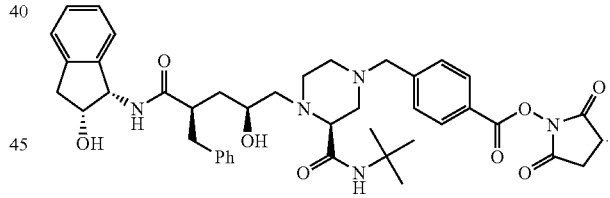

19. A compound having the formula:

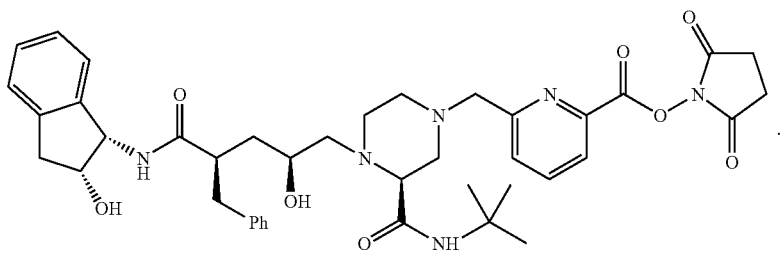

20. A compound having the formula:

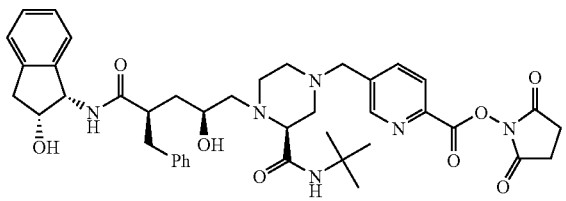

21. A compound having formula:

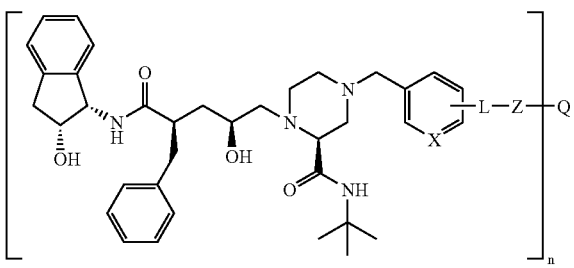

where X is N or C, L is a linking group comprising 1 to 40 carbon atoms arranged in a straight or a branched chain, saturated or unsaturated, and further comprising up to two ring structures and 0–20 heteroatoms, with the proviso that not more than two heteroatoms may be linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

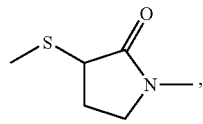

Q is selected from the group consisting of polypeptides, polysaccharides, synthetic polymers, and non-isotopic labels, and n is a number from 1 to 50 per 50 kilodaltons molecular weight of Q.

22. A compound having the formula:

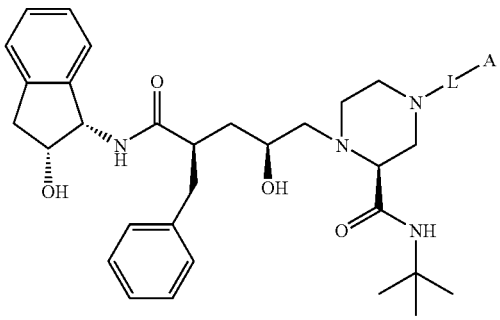

where L is an aliphatic linking group comprising 1 to 40 carbon atoms arranged in a straight or a branched chain, saturated or unsaturated, and 0–20 heteroatoms, with the proviso that not more than two heteroatoms may be linked in sequence, and A is an activated functionality selected from the group consisting of active esters, isocyanates, isothiocyanates, thiols, imidoesters, anhydrides, maleimides, thiolactones, diazonium groups, and aldehydes.

23. A compound having the formula:

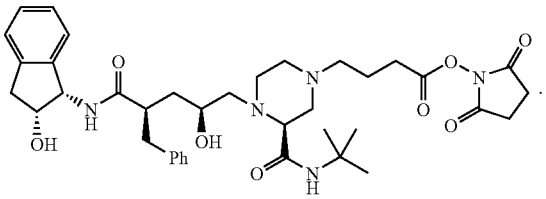

24. A compound having the formula:

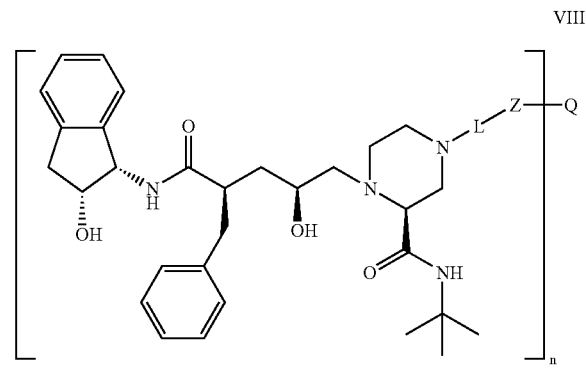

where L is an aliphatic linking group comprising 1 to 40 carbon atoms arranged in a straight or a branched chain, saturated or unsaturated, and further comprising 0–20 heteroatoms, with the proviso that not more than two heteroatoms may be linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

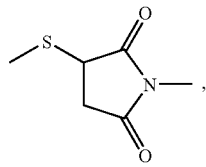

Q is selected from the group consisting of polypeptides, polysaccharides, synthetic polymers, and non-isotopic labels, and n is a number from 1 to 50 per 50 kilodaltons molecular weight of Q.

25. A method for the synthesis of indinavir M6 comprising the step of reacting indinavir sulfate in the presence of hydrogen gas and palladium catalyst whereby indinavir M6 is formed.

26. An assay method for determining indinavir in a sample comprising the steps of:
  combining a sample suspected of containing indinavir with an antibody specific for indinavir and a conjugate comprising an analog of indinavir and a non-isotopic label wherein a signal is generated when the antibody binds with indinavir in the sample, the conjugate having the formula:

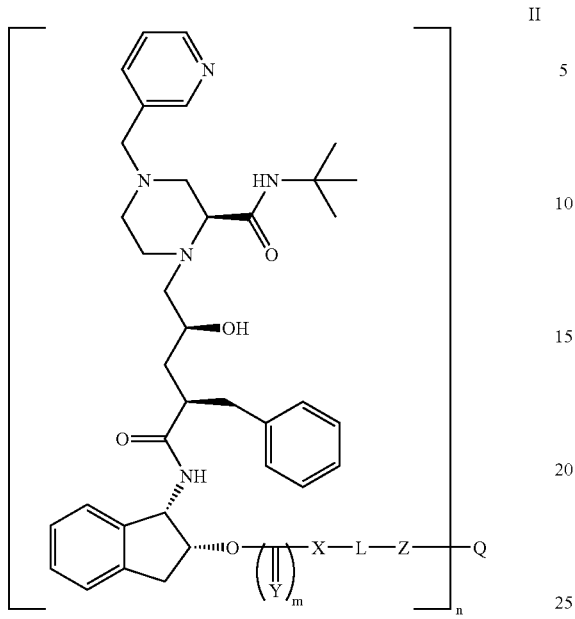

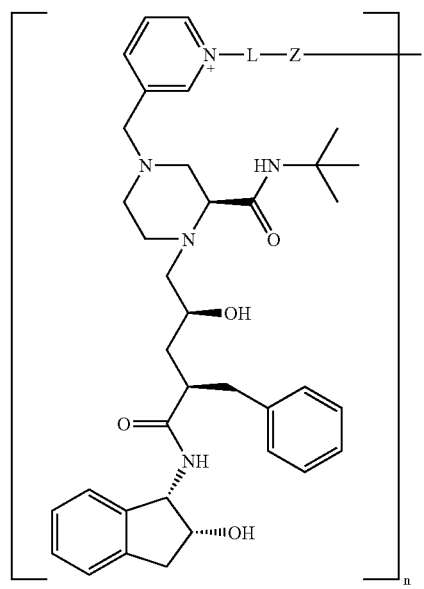

where Y=O or S, m=1, X=CH₂ or NH, L is a linking group comprising 1 to 40 carbon atoms in a straight or a branched chain, saturated or unsaturated, and containing up to two ring structures and 0–20 heteroatoms, and Z is a moiety selected from the group consisting of —COHN—, —NHCO—, —NHCONH—, —NHCSNH—, —OCONH—, —NHOCO—, —S—, —NH(=NH)—, —N=N—, —NH—, and where L is a linking group comprising 1 to 40 carbon atoms in a straight or a branched chain, saturated or unsaturated, and containing up to two ring structures and 0–20 heteroatoms, and Z is a moiety selected from the group consisting of —CONH—, —NHCO—, —NHCONH—, —NHCSNH—, —OCONH—, —NHOCO—, —S—, —NH(C=NH)—, —NH—, and

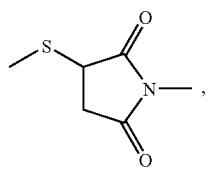

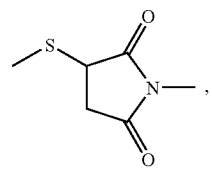

Q is a non-isotopic label, and n is a number from 1 to 50 per 50 kilodaltons molecular weight of Q, measuring the amount of signal generated, and correlating the measured signal with the presence or amount of indinavir in the sample.

27. An assay method for determining indinavir in a sample comprising the steps of:

combining a sample suspected of containing indinavir with an antibody specific for indinavir and a conjugate comprising an analog of indinavir and a non-isotopic label wherein a signal is generated when the antibody binds with indinavir in the sample, the conjugate having the formula Q is a non-isotopic label, and n is a number from 1 to 50 per 50 kilodaltons molecular weight of Q, measuring the amount of signal generated, and correlating the measured signal with the presence or amount of indinavir in the sample.

28. An assay method for determining indinavir in a sample comprising the steps of:

combining a sample suspected of containing indinavir with an antibody specific for indinavir and a conjugate comprising an analog of indinavir and a non-isotopic label wherein a signal is generated when the antibody binds with indinavir in the sample, the conjugate having the formula:

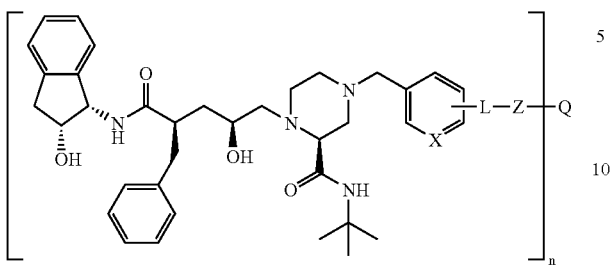

where L is a linking group comprising 1 to 40 carbon atoms in a straight or a branched chain, saturated or unsaturated, and containing up to two ring structures and 0–20 heteroatoms, and Z is a moiety selected from the group consisting of —CONH—, —NHCO—, —NHCONH—, —NHCSNH—, —OCONH—, —NHOCO—, —S—, —NH(C=NH)—, —N=N—, —NH—, and

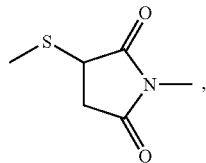

Q is a non-isotopic label, and n is a number from 1 to 50 per 50 kilodaltons molecular weight of Q, measuring the amount of signal generated, and correlating the measured signal with the presence or amount of indinavir in the sample.

* * * * *